(12) United States Patent
Kamei et al.

(10) Patent No.: US 11,144,024 B2
(45) Date of Patent: Oct. 12, 2021

(54) INSIDE AIR CONTROL SYSTEM

(71) Applicant: DAIKIN INDUSTRIES, LTD., Osaka (JP)

(72) Inventors: Noritaka Kamei, Osaka (JP); Yuusuke Fujimoto, Osaka (JP); Naoki Nakatani, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 17/319,284

(22) Filed: May 13, 2021

(65) Prior Publication Data

US 2021/0263492 A1 Aug. 26, 2021

Related U.S. Application Data

(63) Continuation of application No. PCT/JP2019/040892, filed on Oct. 17, 2019.

(30) Foreign Application Priority Data

Nov. 14, 2018 (JP) .............................. JP2018-213590

(51) Int. Cl.
*G01N 33/00* (2006.01)
*G05B 19/042* (2006.01)
(Continued)

(52) U.S. Cl.
CPC .......... *G05B 19/042* (2013.01); *A23B 7/0425* (2013.01); *A23B 7/148* (2013.01);
(Continued)

(58) Field of Classification Search
CPC .......... G05B 19/042; G05B 2219/2614; G01N 33/004; G01N 33/007; G01N 33/0006;
(Continued)

(56) References Cited

U.S. PATENT DOCUMENTS 5,457,963 A 10/1995 Cahill-O'Brien et al.
2017/0003258 A1* 1/2017 Krauss ................. G01N 21/274
(Continued)

FOREIGN PATENT DOCUMENTS

JP 8-168 A 1/1996
JP 2005-83896 A 3/2005
JP 2006-153601 A 6/2006
(Continued)

OTHER PUBLICATIONS

English translation of International Preliminary Report on Patentability and Written Opinion of the International Searching Authority for International Application No. PCT/JP2019/040892, dated May 27, 2021.
(Continued)

*Primary Examiner* — Kenneth M Lo
*Assistant Examiner* — Michael W Choi
(74) *Attorney, Agent, or Firm* — Birch, Stewart, Kolasch & Birch, LLP

(57) ABSTRACT

A carbon dioxide sensor (92) measures the carbon dioxide concentration of inside air. An inside air control system (30) controls the carbon dioxide concentration of the inside air based on a measured value obtained by the carbon dioxide sensor (92). If the measured value obtained by the carbon dioxide sensor (92) returns to a predetermined normal range after falling outside the normal range, the controller (110) of the inside air control system (30) performs a determination operation. The determination operation is an operation for supplying outdoor air to the carbon dioxide sensor (92) to determine whether or not the carbon dioxide sensor (92) is normal.

9 Claims, 10 Drawing Sheets

(51) Int. Cl.
  *A23B 7/04* (2006.01)
  *A23B 7/148* (2006.01)
  *F25D 11/00* (2006.01)
(52) U.S. Cl.
  CPC ....... *G01N 33/004* (2013.01); *G01N 33/0006* (2013.01); *G01N 33/007* (2013.01); *A23V 2002/00* (2013.01); *F25D 11/003* (2013.01); *G05B 2219/2614* (2013.01)
(58) Field of Classification Search
  CPC ..... A23B 7/148; A23B 7/0425; F25D 11/003; A23V 2002/00
  See application file for complete search history.

(56) References Cited

U.S. PATENT DOCUMENTS

2017/0355518 A1* 12/2017 Zita ................. A23B 7/148
2018/0038625 A1   2/2018 Yokohara et al.
2019/0294136 A1*  9/2019 Iacobone ........... G05B 19/0428

FOREIGN PATENT DOCUMENTS

| JP | 2009-174937 A | 8/2009 |
| JP | 2016-164485 A | 9/2016 |
| JP | 2018-148877 A | 9/2018 |

OTHER PUBLICATIONS

International Search Report, issued in PCT/JP2019/040892, PCT/ISA/210, dated Dec. 10, 2019.

* cited by examiner

INSIDE AIR CONTROL SYSTEM

CROSS REFERENCE TO RELATED APPLICATIONS

This application is a Continuation of PCT International Application No. PCT/JP2019/040892 filed on Oct. 17, 2019, which claims priority under 35 U.S.C. § 119(a) to Patent Application No. 2018-213590 filed in Japan on Nov. 14, 2018, all of which are hereby expressly incorporated by reference into the present application.

TECHNICAL FIELD

The present disclosure relates to an inside air control system.

BACKGROUND ART

Patent Document 1 discloses an inside air control system that controls the composition of inside air in a storage, such as a shipping container. To keep vegetables, fruits, and other items stored in the storage fresh, this inside air control system mainly controls the oxygen concentration and carbon dioxide concentration of the inside air. This inside air control system includes an oxygen sensor and a carbon dioxide sensor as gas sensors each of which measures the concentration of an associated gas contained in the inside air. The oxygen sensor measures the oxygen concentration of the inside air. The carbon dioxide sensor measures the carbon dioxide concentration of the inside air. Thus, this inside air control system controls the composition of the inside air using measured values measured by the sensors.

CITATION LIST

Patent Document

Patent Document 1: Japanese Unexamined Patent Publication No. 2018-148877

SUMMARY

A first aspect of the present disclosure is directed to an inside air control system including: a gas sensor (92) configured to measure a concentration of a target gas contained in inside air in a storage (1). The inside air control system performs a concentration control operation to control the concentration of the target gas in the inside air based on a measured value obtained by the gas sensor (92). The inside air control system further includes: an outdoor air supply passage (255, 281) through which outdoor air is to be supplied to the gas sensor (92); and a controller (110) configured to perform a determination operation if the measured value obtained by the gas sensor (92) returns to a predetermined normal range after falling outside the normal range. The determination operation is performed to supply outdoor air through the outdoor air supply passage (255, 281) to the gas sensor (92) to determine whether or not the gas sensor (92) is normal.

DESCRIPTION OF EMBODIMENTS

Embodiments of the present invention will be described in detail with reference to the drawings. An inside air control system (30) according to this embodiment is installed in a shipping container (1) to provide so-called controlled atmosphere (CA) transportation. The inside air control system (30) controls the composition of air in the shipping container (1) such that the composition of the air therein is different from that of the atmosphere.

Figure 1:
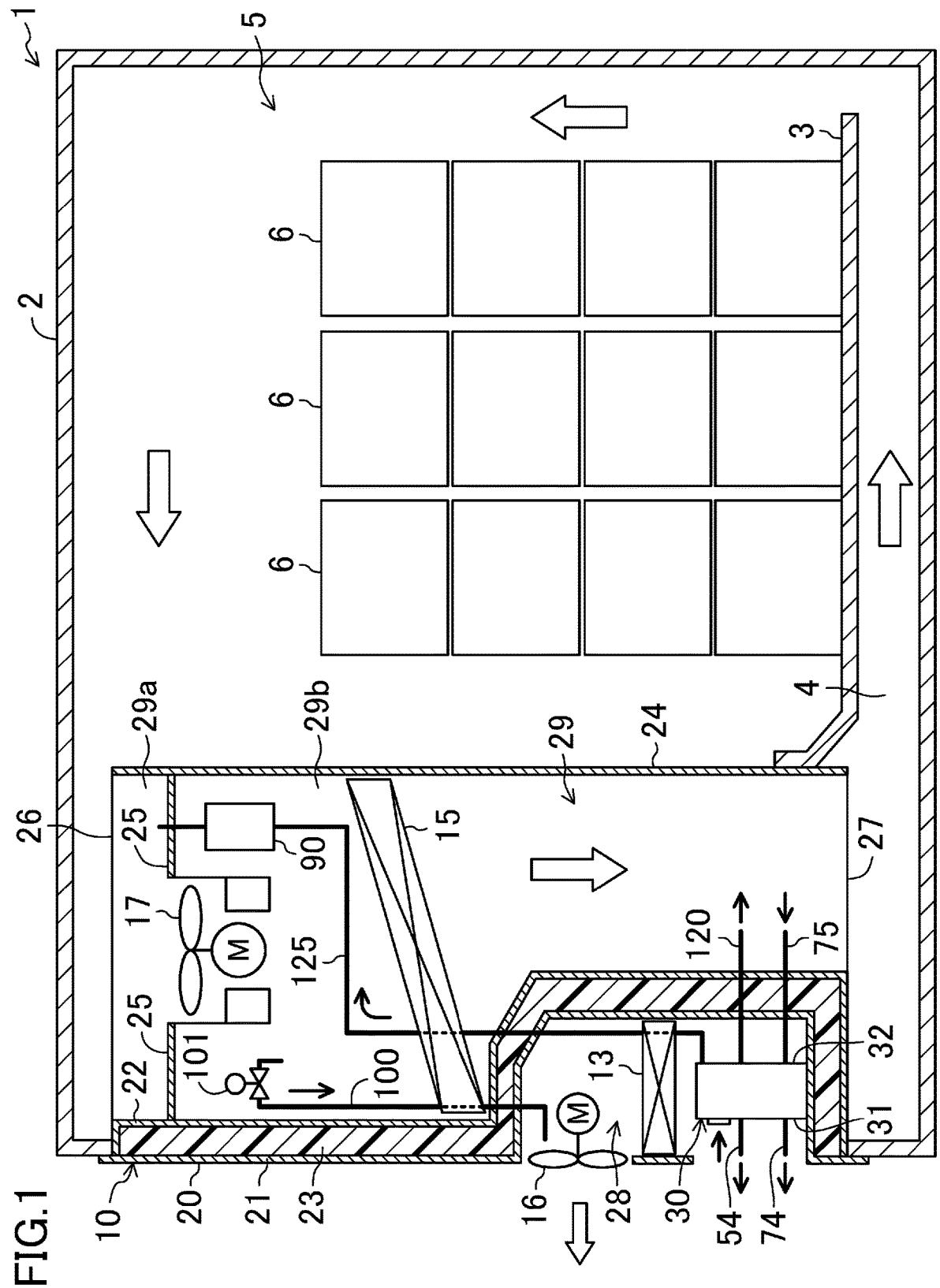
FIG. 1 is a schematic cross-sectional view of a shipping container including an inside air control system according to an embodiment.

As illustrated in FIG. 1, the shipping container (1) constituting a storage includes a container body (2) and a container refrigerator (10). This shipping container (1) is a reefer container capable of controlling the internal temperature thereof. The inside air control system (30) according to this embodiment is installed in the container refrigerator (10). This shipping container (1) is used to transport plants, which breathe by absorbing oxygen ($O_2$) in the air and releasing carbon dioxide ($CO_2$) into the air. Examples of such plants include fruits, such as bananas and avocados, vegetables, cereals, bulbous plants, and natural flowers.

The container body (2) has the shape of an elongated rectangular parallelepiped box. The container body (2) has an open end surface. The container refrigerator (10) is attached to the container body (2) to close the open end of the container body (2). The internal space of the container body (2) constitutes a cargo space (5) for storing cargos (6).

A floorboard (3) on which the cargos (6) are to be placed is disposed at the bottom of the cargo space (5). An underfloor path (4) is formed between the floorboard (3) and a bottom plate of the container body (2) to allow air blown by the container refrigerator (10) to flow therethrough. The underfloor path (4) extends along the bottom plate of the container body (2) in the longitudinal direction of the container body (2). The underfloor path (4) has one end connected to a blowout port (27) of the container refrigerator (10), and the other end communicating with a space above the floorboard (3) (i.e., a space in which the cargos (6) are housed).

—Container Refrigerator—

As illustrated in FIG. 1, the container refrigerator (10) includes a casing (20), a refrigerant circuit (11) that performs a refrigeration cycle, an external fan (16), and an internal fan (17).

The casing (20) includes an external wall (21), an internal wall (22), a backboard (24), and a partition board (25). As will be described below, this casing (20) is provided with the refrigerant circuit (11), the external fan (16), and the internal fan (17).

The external wall (21) is a plate-shaped member positioned to cover the open end of the container body (2). The external wall (21) has a lower portion protruding into the container body (2). The internal wall (22) is a plate-shaped member with a shape that conforms to that of the external wall (21). The internal wall (22) is positioned to cover a surface of the external wall (21) near the inside of the container body (2). A thermal insulator (23) fills the space between the external and internal walls (21) and (22).

The casing (20) has a lower portion recessed toward the inside of the container body (2). The lower portion of the casing (20) forms an external equipment room (28) communicating with a space outside the shipping container (1). The external fan (16) is disposed in the external equipment room (28).

The backboard (24) is a substantially rectangular flat plate-shaped member. The backboard (24) is positioned closer to the inside of the container body (2) than the internal wall (22) is. An inside air flow path (29) is formed between the backboard (24) and the internal wall (22). This inside air flow path (29) has an upper end forming an intake port of the casing (20), and a lower end forming the blowout port (27) of the casing (20).

The partition board (25) is a plate-shaped member positioned to partition the inside air flow path (29) into upper and lower sections. The partition board (25) is disposed in an upper portion of the inside air flow path (29). This partition board (25) partitions the inside air flow path (29) into a primary flow path (29a) above the partition board (25) and a secondary flow path (29b) below the partition board (25). The primary flow path (29a) communicates with the cargo space (5) via the intake port (26). The secondary flow path (29b) communicates with the underfloor path (4) via the blowout port (27). The internal fan (17) is attached to the partition board (25). The internal fan (17) is positioned to blow air sucked from the primary flow path (29a) to the secondary flow path (29b).

Figure 2:
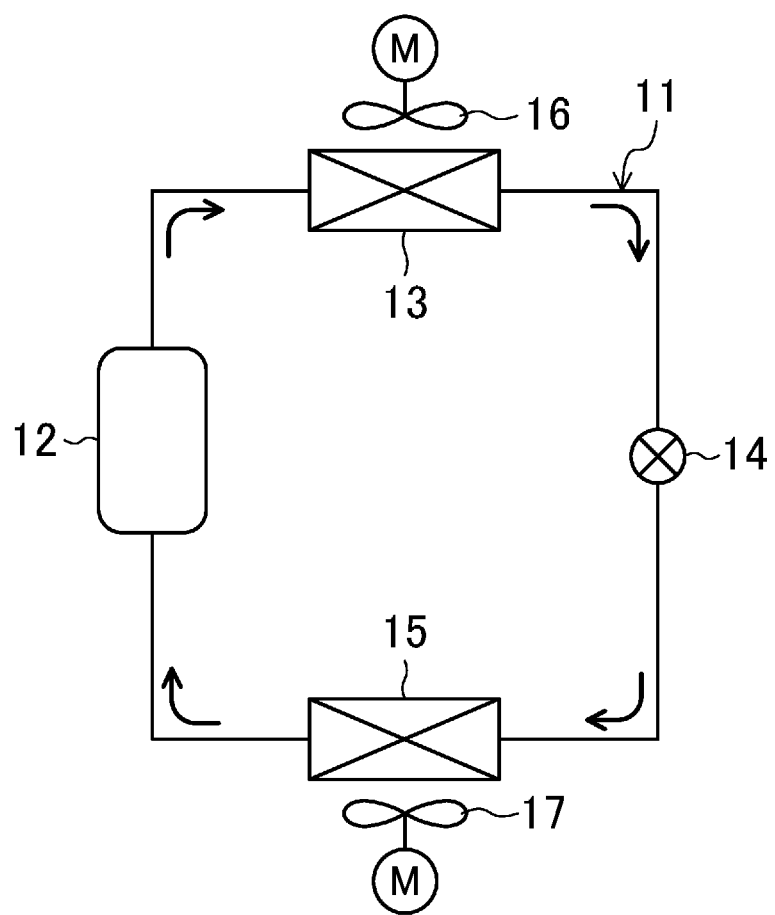
FIG. 2 is a refrigerant circuit diagram illustrating a configuration of a refrigerant circuit of a container refrigerator installed in a shipping container.

As shown in FIG. 2, the refrigerant circuit (11) is a closed circuit in which a compressor (12), a condenser (13), an expansion valve (14), and an evaporator (15) are connected together in this order by piping. Actuating the compressor (12) allows a refrigerant to circulate through the refrigerant circuit (11), which performs a vapor compression refrigeration cycle. As illustrated in FIG. 1, the condenser (13) is disposed in a portion of the external equipment room (28) on the suction side of the external fan (16), and the evaporator (15) is disposed in the secondary flow path (29b) of the inside air flow path (29). Although not shown in FIG. 1, the compressor (12) is disposed in the external equipment room (28).

—Inside Air Control System—

As illustrated in FIG. 1, the inside air control system (30) is provided with a main unit (31), a sensor unit (90), a ventilation exhaust pipe (100), and a controller (110). The main unit (31) is installed in the external equipment room (28) of the container refrigerator (10). The sensor unit (90) is installed in the inside air flow path (29) of the shipping container (1). The ventilation exhaust pipe (100) is installed astride the inside air flow path (29) and external equipment room (28) of the shipping container (1). The controller (110) is provided in the main unit (31) to control components of the inside air control system (30). The sensor unit (90), the ventilation exhaust pipe (100), and the controller (110) will be described in detail below.

Figure 3:
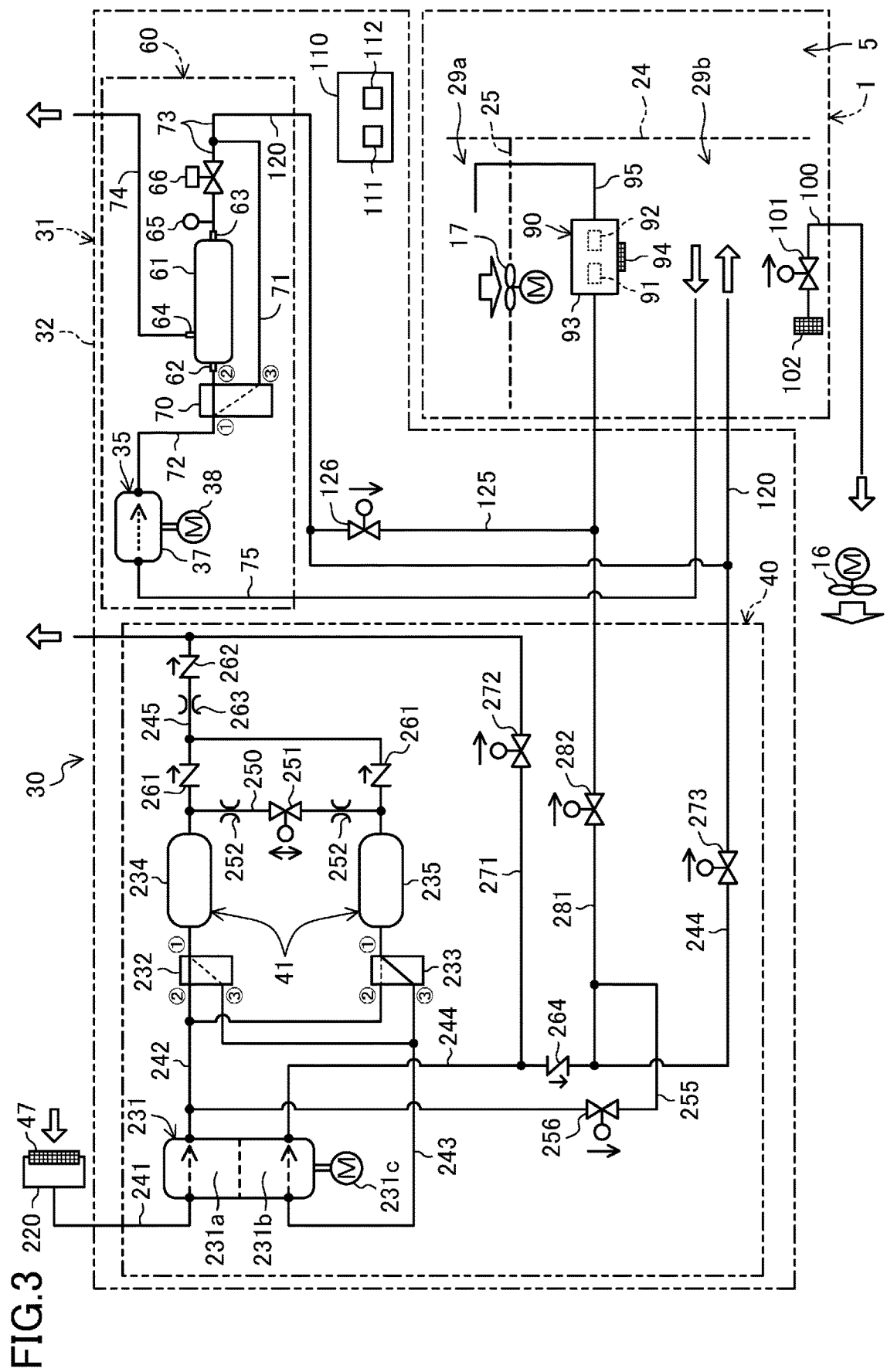
FIG. 3 is a piping system diagram showing a configuration of an inside air control system according to an embodiment.

As illustrated in FIG. 3, the main unit (31) of the inside air control system (30) includes a first composition controller (40), a second composition controller (60), and a unit case (32). The unit case (32) is a closed container in the shape of a box. The first and second composition controllers (40) and (60) are arranged in the internal space of the unit case (32). The first and second composition controllers (40) and (60) will be described in detail below.

The inside air control system (30) includes a supply pipe (120), an internal suction pipe (75), and a measurement pipe (125). The supply pipe (120), the internal suction pipe (75), and the measurement pipe (125) are used to connect the main unit (31) to the inside air flow path (29) of the container refrigerator (10).

The supply pipe (120) is used to supply air that has flowed out of the first and second composition controllers (40) and (60) to the cargo space (5). The supply pipe (120) has an intake port end connected to the first and second composition controllers (40) and (60), and a blowout port end opening into the secondary flow path (29b) of the inside air flow path (29).

The internal suction pipe (75) is used to supply inside air in the cargo space (5) to the second composition controller (60). The internal suction pipe (75) has an intake port end opening into the secondary flow path (29b) of the inside air flow path (29), and an blowout port end connected to a pump body (37) of the second composition controller (60) described below. The intake port end of the internal suction pipe (75) is disposed in a portion of the secondary flow path (29b) of the inside air flow path (29) upstream of the blowout port end of the supply pipe (120).

The measurement pipe (125) is used to supply air flowing through the supply pipe (120) to the sensor unit (90). The measurement pipe (125) has an intake port end connected to the supply pipe (120), and an blowout port end connected to the sensor unit (90). The measurement pipe (125) is provided with a second measurement on-off valve (126) configured as an electromagnetic valve. The second measurement on-off valve (126) is housed in the unit case (32) of the main unit (31).

Note that the ventilation exhaust pipe (100), the supply pipe (120), the internal suction pipe (75), the measurement pipe (125), and pipes of the composition controllers (40, 60) described below may be each configured as a hard pipe, a flexible hose, or a combination of a pipe and a hose.

—First Composition Controller—

The first composition controller (40) is configured to separate outside air (untreated outside air) sucked from the outside of the shipping container (1) into a first type of outside air and a second type of outside air. This first composition controller (40) is configured to separate such untreated outside air into the first type of outside air and the second type of outside air by so-called pressure swing adsorption (PSA).

The first type of outside air has a higher nitrogen concentration and a lower oxygen concentration than untreated outside air. The second type of outside air has a lower nitrogen concentration and a higher oxygen concentration than untreated outside air. As can be seen, the first and second types of outside air differ from each other in the concentrations of their constituent substances therein. Note that the "concentration" as used herein means the proportion in volume.

The first composition controller (40) includes an air pump (231). The first composition controller (40) further includes first and second directional control valves (232) and (233), and first and second adsorption columns (234) and (235). As will be described below, the adsorption columns (234, 235) each include an adsorbent that adsorbs nitrogen in air.

<Air Pump>

The air pump (231) is disposed in the internal space of the unit case (32). The air pump (231) includes first and second pump mechanisms (231a) and (231b), each of which sucks and compresses the air and discharges the compressed air. The first and second pump mechanisms (231a) and (231b) are oil-free pumps without lubricant. The first pump mechanism (231a) serving as a pressurizing portion and the second pump mechanism (231b) serving as a depressurizing portion are both connected to a drive shaft of a motor (231c). The first and second pump mechanisms (231a) and (231b) are each driven in rotation by the motor (231c) to suck the air through its intake port, compress the sucked air, and discharge the compressed air through its blowout port.

<Outdoor Air Pipe, Discharge Pipe, Filter Unit>

The intake port of the first pump mechanism (231a) is connected to one end of an outdoor air pipe (241) defining an outdoor air passage. The outdoor air pipe (241) is arranged to pass through the unit case (32). The other end of the outdoor air pipe (241) located outside the unit case (32) is connected to a filter unit (220).

The filter unit (220) includes an air filter (47). The air filter (47) is used to capture dust, salt, and other substances contained in outside air. In this embodiment, an air-permeable, waterproof membrane filter is used as the air filter (47). The filter unit (220) is a box-shaped member, and introduces air (outside air) that has passed through the air filter (47) into the outdoor air pipe (241). Although not shown, the filter unit (220) is disposed in a portion of the external equipment room (28) downstream of the condenser (13).

The blowout port of the first pump mechanism (231a) is connected to one end of a discharge pipe (242) defining a discharge passage. The discharge pipe (242) branches into two branch pipes near the other end thereof. One of the branch pipes is connected to the first directional control valve (232), and the other branch pipe is connected to the second directional control valve (233).

<Suction Pipe, Supply Pipe>

The intake port of the second pump mechanism (231b) is connected to one end of a suction pipe (243) defining a suction passage. The suction pipe (243) branches into two branch pipes near the other end thereof. One of the branch pipes is connected to the first directional control valve (232), and the other branch pipe is connected to the second directional control valve (233).

The blowout port of the second pump mechanism (231b) is connected to one end of a supply connection pipe (244) defining a supply passage. The other end of the supply connection pipe (244) is connected to the supply pipe (120).

The supply connection pipe (244) is provided with a check valve (264) and a supply on-off valve (273) in this order from the one end to the other end thereof. The check valve (264) allows the air to flow only from the one end to the other end of the supply connection pipe (244), and prevents backflow of the air. The supply on-off valve (273) is an on-off valve configured as an electromagnetic valve.

<Directional Control Valves>

The first and second directional control valves (232) and (233) are switching valves each having three ports. The directional control valves (232, 233) are each configured to switch between a first state where a first port communicates with a second port so as to be blocked from a third port and a second state where the first port communicates with the third port so as to be blocked from the second port.

The first directional control valve (232) has its first port connected to one end of the first adsorption column (234). The first directional control valve (232) has its second port connected to the associated branch pipe of the discharge pipe (242), and has its third port connected to the associated branch pipe of the suction pipe (243). The first directional control valve (232) switches between a state where the first adsorption column (234) is allowed to communicate with the first pump mechanism (231a), and a state where the first adsorption column (234) is allowed to communicate with the second pump mechanism (231b).

The second directional control valve (233) has its first port connected to one end of the second adsorption column (235). The second directional control valve (233) has its second port connected to the associated branch pipe of the discharge pipe (242), and has its third port connected to the associated branch pipe of the suction pipe (243). The second directional control valve (233) switches between a state where the second adsorption column (235) is allowed to communicate with the first pump mechanism (231a), and a state where the second adsorption column (235) is allowed to communicate with the second pump mechanism (231b).

<Adsorption Columns>

The first and second adsorption columns (234) and (235) are members each including a cylindrical container with both ends closed and an adsorbent that fills the container.

The adsorbent that fills these adsorption columns (234, 235) adsorbs a nitrogen component in a state where the adsorption columns (234, 235) are pressurized to have a higher pressure than the atmospheric pressure, and desorbs the nitrogen component in a state where the adsorption columns (234, 235) are depressurized to have a lower pressure than the atmospheric pressure. Examples of the adsorbent to be used in this embodiment include porous zeolite having pores with a diameter smaller than the diameter of nitrogen molecules (3.0 angstrom) and larger than the diameter of oxygen molecules (2.8 angstrom).

The first and second adsorption columns (234) and (235) of the first composition controller (40) of this embodiment form a first separator (41). The two adsorption columns (234, 235) forming the first separator (41) separate untreated outside air into the first type of outside air having a higher nitrogen concentration and a lower oxygen concentration than the untreated outside air, and the second type of outside air having a lower nitrogen concentration and a higher oxygen concentration than the untreated outside air.

<Oxygen Discharge Pipe>

An oxygen discharge pipe (245) defining an oxygen discharge passage branches into two branch pipes near one end thereof. One of the branch pipes is connected to the other end of the first adsorption column (234), and the other branch pipe is connected to the second adsorption column (235). Each of the branch pipes of the oxygen discharge pipe (245) is provided with one check valve (261). Each of the check valves (261) allows the air to flow in a direction in which the air flows out of the associated adsorption column (234, 235), and prevents backflow of the air.

The oxygen discharge pipe (245) is arranged to pass through the unit case (32). The other end of the oxygen discharge pipe (245) opens into a space outside the shipping container (1). A joined portion of the oxygen discharge pipe (245) is provided with a check valve (262) and an orifice (263). The check valve (262) is disposed closer to the other end of the oxygen discharge pipe (245) than the orifice (263) is. The check valve (262) allows the air to flow toward the other end of the oxygen discharge pipe (245), and prevents backflow of the air.

<Purge Pipe>

The branch pipes of the oxygen discharge pipe (245) are connected to a purge pipe (250) defining a purge passage. The purge pipe (250) has one end connected to one of the branch pipes connected to the first adsorption column (234), and the other end connected to the other branch pipe connected to the second adsorption column (235). The one end of the purge pipe (250) is connected between the first adsorption column (234) and the associated check valve (261). The other end of the purge pipe (250) is connected between the second adsorption column (235) and the associated check valve (261).

The purge pipe (250) is provided with a purge valve (251). The purge valve (251) is an on-off valve configured as an electromagnetic valve. The purge valve (251) is opened to equalize the pressures of the first and second adsorption columns (234) and (235). Portions of the purge pipe (250) on both sides of the purge valve (251) each have an orifice (252).

<Exhaust Connection Pipe>

The supply connection pipe (244) is connected to an exhaust connection pipe (271) defining an exhaust connection passage. The exhaust connection pipe (271) has one end connected to the supply connection pipe (244), and the other end connected to the oxygen discharge pipe (245). The one end of the exhaust connection pipe (271) is connected to a portion of the supply connection pipe (244) between the second pump mechanism (231b) and the check valve (264). The other end of the exhaust connection pipe (271) is connected to a portion of the oxygen discharge pipe (245) closer to the outside of the container than the check valve (262).

The exhaust connection pipe (271) is provided with an exhaust on-off valve (272). The exhaust on-off valve (272) is an on-off valve configured as an electromagnetic valve. The exhaust on-off valve (272) is opened to discharge air flowing through the supply connection pipe (244) to the outside of the container.

<Measurement Connection Pipe>

The supply connection pipe (244) is connected to a measurement connection pipe (281) defining a measurement passage. The measurement connection pipe (281) is used to connect the first composition controller (40) to the sensor unit (90). The measurement connection pipe (281) and a first bypass pipe (255) described below define an outdoor air supply passage through which outside air (outdoor air) is to be supplied to the sensor unit (90).

The measurement connection pipe (281) has one end connected to the supply connection pipe (244), and the other end connected to the measurement pipe (125). The one end of the measurement connection pipe (281) is connected to a portion of the supply connection pipe (244) between the check valve (264) and the supply on-off valve (273). The other end of the measurement connection pipe (281) is connected to a portion of the measurement pipe (125) between the second measurement on-off valve (126) and the sensor unit (90).

The measurement connection pipe (281) is provided with a first measurement on-off valve (282). The first measurement on-off valve (282) is an on-off valve configured as an electromagnetic valve. The first measurement on-off valve (282) is opened to send air flowing through the supply connection pipe (244) or the first bypass pipe (255) described below to the sensor unit (90).

<First Bypass Pipe, First Bypass Valve>

The discharge pipe (242) is connected to the first bypass pipe (255) defining a bypass passage. The first bypass pipe (255) has one end connected to the discharge pipe (242), and the other end connected to the measurement connection pipe (281). The one end of the first bypass pipe (255) is connected to a portion of the discharge pipe (242) closer to the first pump mechanism (231a) than the junction of the two branch pipes of the discharge pipe (242) is. The other end of the first bypass pipe (255) is connected to a portion of the measurement connection pipe (281) between the one end of the measurement connection pipe (281) and the first measurement on-off valve (282). The first bypass pipe (255) defines a first bypass passage through which outside air is to be supplied to the internal space of the shipping container (1) with the first and second adsorption columns (234) and (235) bypassed.

The first bypass pipe (255) is provided with a first bypass valve (256). The first bypass valve (256) is an on-off valve configured as an electromagnetic valve. The first bypass valve (256) constitutes a first bypass valve mechanism for changing the flow rate of outside air flowing into the first bypass pipe (255). This first bypass valve (256) is opened to supply outside air discharged by the first pump mechanism (231a) to the cargo space (5) without changing the composition of the outside air.

—Second Composition Controller—

The second composition controller (60) is configured to separate inside air (untreated inside air) sucked from the internal space of the shipping container (1) into a first type of inside air and a second type of inside air. The second composition controller (60) according to this embodiment supplies the first type of inside air to the cargo space (5), and discharges the second type of inside air as discharge air to the outside of the shipping container (1).

The second composition controller (60) includes a pump unit (35), a separation module (61), a second bypass valve (70), a pressure sensor (65), and a regulating valve (66). The second composition controller (60) further includes an introduction pipe (72), a primary pipe (73), a secondary pipe (74), and a second bypass pipe (71).

<Pump Unit>

The pump unit (35) includes a pump body (37) and a drive motor (38). The pump body (37) is an air pump that discharges sucked air, and is configured as, for example, a positive-displacement fluid machine. The drive motor (38) is an electric motor coupled to the pump body (37). The drive motor (38) drives the pump body (37).

<Separation Module>

The separation module (61) has an introduction port (62), a primary exhaust port (63), and a secondary exhaust port (64). The detailed structure of the separation module (61) will be described below.

The introduction port (62) is connected through the introduction pipe (72) to a blowout port of the pump body (37). The primary exhaust port (63) is connected through the primary pipe (73) to the supply pipe (120). The secondary exhaust port (64) is connected to one end of the secondary pipe (74). The secondary pipe (74) extends to the outside of the unit case (32). The other end of the secondary side pipe

(74) opens into a portion of the external equipment room (28) on the suction side of the external fan (16). An intake port of the pump body (37) is connected to the internal suction pipe (75).

The separation module (61) constitutes a second separator. As will be described in detail below, the separation module (61) includes gas separation membranes (85). The separation module (61) separates the untreated inside air into the first type of inside air that has not permeated the gas separation membranes (85) and the second type of inside air that has permeated the gas separation membranes (85).

The first type of inside air has a higher nitrogen concentration, a lower oxygen concentration, and a lower carbon dioxide concentration than the untreated inside air. The second type of inside air has a lower nitrogen concentration, a higher oxygen concentration, and a higher carbon dioxide concentration than the untreated inside air. As can be seen, the first and second types of inside air differ from each other in the concentrations of their constituent substances therein.

<Second Bypass Valve, Second Bypass Pipe>

The second bypass valve (70) is a switching valve having three ports, and constitutes a second bypass valve mechanism. The second bypass valve (70) is configured to switch between a first state where a first port communicates with a second port so as to be blocked from a third port (the state indicated by the solid line in FIG. 3) and a second state where the first port communicates with the third port so as to be blocked from the second port (the state indicated by the broken line in FIG. 3).

The second bypass valve (70) is disposed somewhere along the introduction pipe (72). The second bypass valve (70) has its first port connected to the blowout port of the pump body (37), and has its second port connected to the introduction port (62) of the separation module (61). The third port of the second bypass valve (70) is connected to the intake port end of the second bypass pipe (71). The blowout port end of the second bypass pipe (71) is connected to the primary pipe (73). The second bypass pipe (71) defines a second bypass passage.

<Second Pressure Sensor, Second Regulating Valve>

The pressure sensor (65) and the regulating valve (66) are provided for the primary pipe (73). The pressure sensor (65) and the regulating valve (66) are disposed closer to the separation module (61) than the other end of the second bypass pipe (71) connected to the primary pipe (73) is. The pressure sensor (65) is disposed closer to the separation module (61) than the regulating valve (66) is.

The pressure sensor (65) measures the pressure of the second type of inside air that has flowed out of the primary exhaust port (63) of the separation module (61). The measured value obtained by the pressure sensor (65) is substantially equal to the pressure of the untreated inside air supplied to the separation module (61) by the pump body (37).

The regulating valve (66) is a motor-operated valve with a variable opening degree, and constitutes a second valve mechanism. Changing the opening degree of the regulating valve (66) triggers a change in the pressure of the untreated inside air supplied to the separation module (61) by the pump body (37).

—Second Separation Module—

Figure 4:
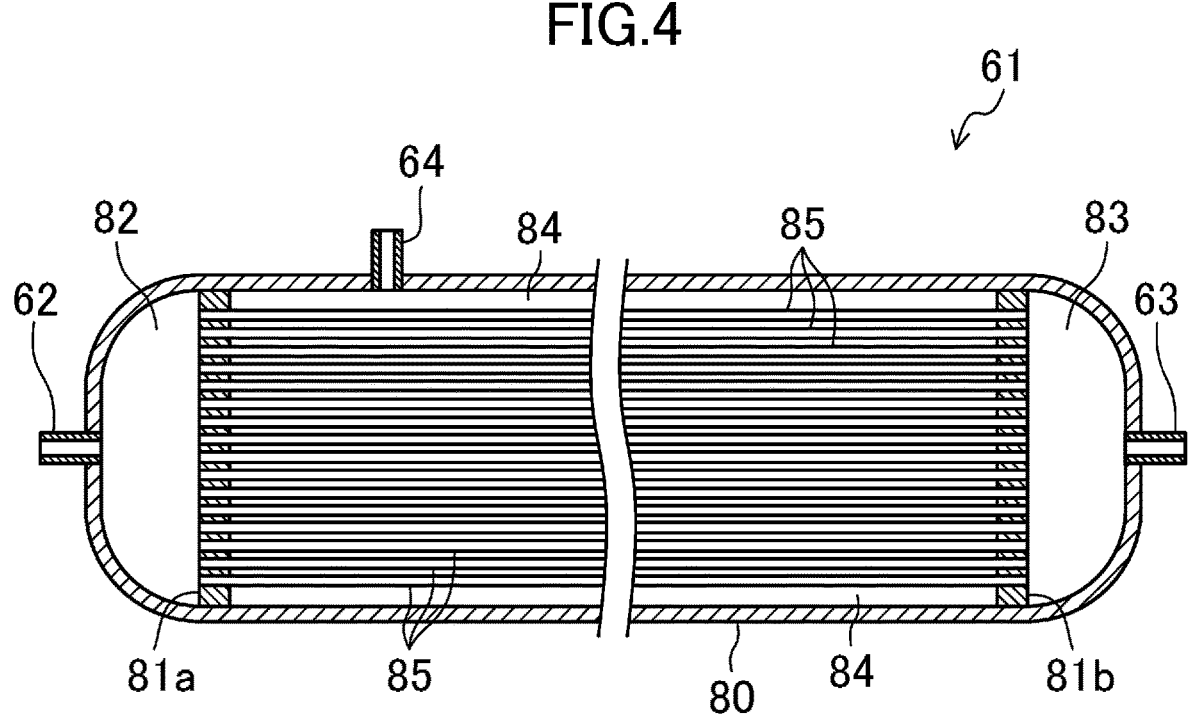
FIG. 4 is a schematic cross-sectional view of a separation module of an inside air control system according to an embodiment.

The separation module (61) will be described with reference to FIG. 4.

The separation module (61) includes one cylindrical case (80) and two partition walls (81a, 81b). The cylindrical case (80) is an elongated cylindrical container with both ends closed. The partition walls (81a, 81b) are members for partitioning the internal space of the cylindrical case (80), and cross the internal space of the cylindrical case (80). The partition walls (81a, 81b) are respectively arranged near two ends of the internal space of the cylindrical case (80). In FIG. 4, the internal space of the cylindrical case (80) is partitioned into an introduction chamber (82) located on the left side of the left partition wall (81a), a secondary exhaust chamber (84) located between the two partition walls (81a, 81b), and a primary exhaust chamber (83) located on the right side of the right partition wall (81b).

The separation module (61) includes the many gas separation membranes (85) formed in the shape of hollow fibers (i.e., in the shape of very thin tubes with an outside diameter of 1 mm or less). The gas separation membranes (85) in the shape of hollow fibers extend from one of the partition walls (81a) to the other partition wall (81b). One end portion of each gas separation membrane (85) passes through the one of the partition walls (81a), and opens into the introduction chamber (82). The other end portion thereof passes through the other partition wall (81b), and opens into the primary exhaust chamber (83). A portion of the internal space of the cylindrical case (80) located between the two partition walls (81a, 81b) and outside the gas separation membranes (85) constitutes a secondary exhaust chamber (84). In the separation module (61), the instruction chamber (82) and the primary exhaust chamber (83) communicate with each other through the gas separation membranes (85) in the shape of hollow fibers, whereas the secondary exhaust chamber (84) does not communicate with spaces inside the gas separation membranes (85), the introduction chamber (82), and the primary exhaust chamber (83).

The cylindrical case (80) is provided with the introduction port (62), the primary exhaust port (63), and the secondary exhaust port (64). The introduction port (62) is positioned at the left end of the cylindrical case (80) in FIG. 4, and communicates with the introduction chamber (82). The primary exhaust port (63) is positioned at the right end of the cylindrical case (80) in FIG. 4, and communicates with the primary exhaust chamber (83). The secondary exhaust port (64) is positioned at a longitudinally middle portion of the cylindrical case (80), and communicates with the secondary exhaust chamber (84).

The gas separation membranes (85) are non-porous membranes made of a polymer. Using the fact that the rate (permeation rate) at which molecules permeate through the gas separation membranes (85) varies among substances, the gas separation membranes (85) separate components contained in mixed gas from one another.

The permeation rate of nitrogen through the gas separation membranes (85) of the separation module (61) is lower than the permeation rates of both oxygen and carbon dioxide. The many gas separation membranes (85) in the shape of hollow fibers have substantially the same thickness. Thus, the permeability of nitrogen through the gas separation membranes (85) of the separation module (61) is lower than the permeabilities of both oxygen and carbon dioxide.

In the separation module (61), air that has flowed through the introduction port (62) into the introduction chamber (82) flows through the spaces inside the gas separation membranes (85) in the shape of hollow fibers toward the primary exhaust chamber (83). Part of the air flowing through the spaces inside the gas separation membranes (85) permeates the gas separation membranes (85) to move to the secondary exhaust chamber (84), and the remaining part thereof flows into the primary exhaust chamber (83).

The permeability of nitrogen through the gas separation membranes (85) of the separation module (61) is lower than the permeabilities of oxygen and carbon dioxide. In other words, nitrogen is less likely to permeate the gas separation membranes (85) than oxygen and carbon dioxide. Thus, as the air flowing through the gas separation membranes (85) in the shape of hollow fibers approaches the primary exhaust chamber (83), the nitrogen concentration of the air increases, and the oxygen and carbon dioxide concentrations thereof decrease. Oxygen and carbon dioxide contained in the air flowing through the gas separation membranes (85) in the shape of hollow fibers permeate the gas separation membranes (85) to move to the secondary exhaust chamber (84).

As a result, the air that has flowed into the primary exhaust chamber (83) without permeating the gas separation membranes (85) has a higher nitrogen concentration, a lower oxygen concentration, and a lower carbon dioxide concentration than the air in the introduction chamber (82). The air that has permeated the gas separation membranes (85) to move to the secondary exhaust chamber (84) has a lower nitrogen concentration, a higher oxygen concentration, and a higher carbon dioxide concentration than the air in the introduction chamber (82).

In the separation module (61), untreated inside air flows through the introduction port (62) into the introduction chamber (82). Part of the untreated inside air that has flowed into the primary exhaust chamber (83) without permeating the gas separation membranes (85) flows out of the primary exhaust port (63) as the first type of inside air, and the remaining part of the untreated inside air that has permeated the gas separation membranes (85) to flow into the secondary exhaust chamber (84) flows out of the secondary exhaust port (64) as the second type of inside air.

—Sensor Unit—

As illustrated in FIGS. 1 and 3, the sensor unit (90) is disposed in the secondary flow path (29*b*) of the inside air flow path (29) of the container refrigerator (10). As illustrated in FIG. 3, the sensor unit (90) includes an oxygen sensor (91), a carbon dioxide sensor (92), and a sensor case (93).

The oxygen sensor (91) is a sensor of zirconia current type that measures the oxygen concentration of mixed gas such as air. The carbon dioxide sensor (92) is a non-dispersive infrared (NDIR) sensor that measures the carbon dioxide concentration of the mixed gas such as air. This carbon dioxide sensor (92) is a gas sensor that measures the concentration of carbon dioxide, as a target gas, contained in the inside air. The oxygen sensor (91) and the carbon dioxide sensor (92) are housed in the sensor case (93).

The sensor case (93) is a somewhat elongated box-shaped member. The sensor case (93) has one longitudinal end connected to the blowout port end of the measurement pipe (125), and the other longitudinal end connected to one end of a blowout port pipe (95). The other end of the blowout port pipe (95) opens into the primary flow path (29*a*) of the inside air flow path (29). An air filter (94) is attached to the sensor case (93) to introduce inside air flowing through the inside air flow path (29) into the internal space of the sensor case (93). The air filter (94) is a membrane filter for capturing dust and other substances contained in the inside air.

As will be described below, during operation of the internal fan (17), the air pressure in the secondary flow path (29*b*) is slightly higher than the air pressure in the primary flow path (29*a*). Thus, while the first and second measurement on-off valves (282) and (126) are closed, inside air in the secondary flow path (29*b*) flows through the air filter (94) into the sensor case (93), and then flows through the blowout port pipe (95) into the primary flow path (29*a*). In this state, the oxygen sensor (91) of the sensor unit (90) measures the oxygen concentration of the inside air, and the carbon dioxide sensor (92) thereof measures the carbon dioxide concentration of the inside air.

—Ventilation Exhaust Pipe—

The ventilation exhaust pipe (100) is used to connect the inside and outside of the shipping container (1) together. The ventilation exhaust pipe (100) defines a ventilation exhaust passage. As illustrated in FIG. 1, the ventilation exhaust pipe (100) passes through the casing (20) of the container refrigerator (10). One end of the ventilation exhaust pipe (100) opens into the secondary flow path (29*b*) of the inside air flow path (29). The other end of the ventilation exhaust pipe (100) opens into a portion of the external equipment room (28) on the suction side of the external fan (16).

As illustrated in FIG. 3, an air filter (102) is attached to the one end of the ventilation exhaust pipe (100). The air filter (102) is a membrane filter for capturing dust and other substances contained in the inside air. The ventilation exhaust pipe (100) is provided with a ventilation exhaust valve (101). The ventilation exhaust valve (101) is an on-off valve configured as an electromagnetic valve.

—Controller—

The controller (110) includes a CPU (111) that executes a control operation, and a memory (112) that stores data and other elements necessary for the control operation. The controller (110) receives the measured values obtained by the oxygen sensor (91) and the carbon dioxide sensor (92). The controller (110) is configured to control operation of the inside air control system (30) based on the measured values obtained by the oxygen sensor (91) and the carbon dioxide sensor (92) so as to maintain the oxygen concentration and carbon dioxide concentration of the inside air within their respective target ranges.

Figure 5:
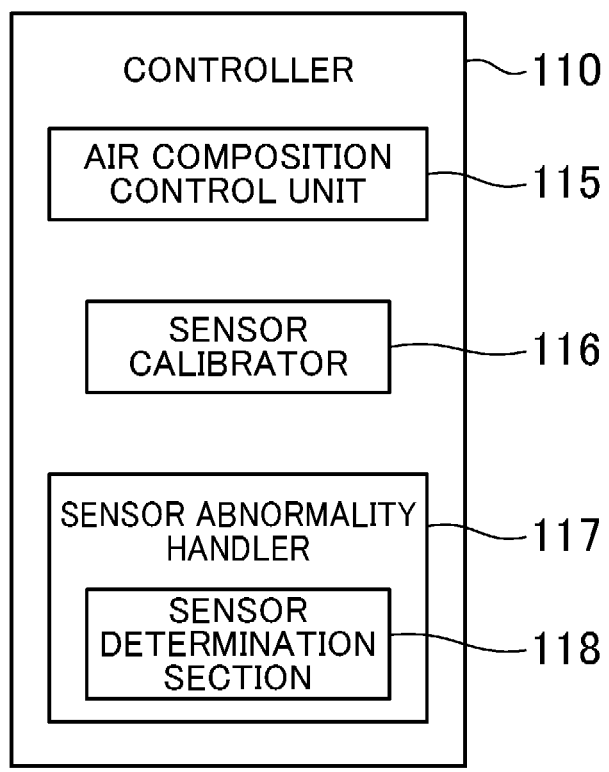
FIG. 5 is a block diagram showing a configuration of a controller of an inside air control system according to an embodiment.

As shown in FIG. 5, the controller (110) includes an air composition control unit (115), a sensor calibrator (116), and a sensor abnormality handler (117). The sensor abnormality handler (117) includes a sensor determiner (118). The air composition control unit (115), the sensor calibrator (116), and the sensor abnormality handler (117) are configured as the CPU (111) that executes a program recorded in the memory (112).

The air composition control unit (115) performs an air composition control operation to control the operation of the inside air control system (30) so that the oxygen concentration and carbon dioxide concentration of the inside air fall within their respective target ranges. The sensor calibrator (116) performs a calibration operation to use outside air (outdoor air) to calibrate the carbon dioxide sensor (92). The sensor abnormality handler (117) performs an abnormality handling operation to handle a situation where the measured value obtained by the carbon dioxide sensor (92) is abnormal. The sensor determiner (118) performs a determination operation to use outside air (outdoor air) to determine whether or not the carbon dioxide sensor (92) is normal. In the abnormality handling operation, the sensor abnormality handler (117) makes the sensor determiner (118) execute the determination operation when a predetermined condition is satisfied.

—Operation of Container Refrigerator—

The container refrigerator (10) performs a cooling operation to cool inside air in the shipping container (1).

In the cooling operation, the compressor (12) of the refrigerant circuit (11) operates to circulate the refrigerant through the refrigerant circuit (11), thereby performing a vapor compression refrigeration cycle. In the refrigerant circuit (11), the refrigerant discharged from the compressor

(12) passes through the condenser (13), the expansion valve (14), and the evaporator (15) in this order, and is then sucked into the compressor (12) so as to be compressed.

In the cooling operation, the external fan (16) and the internal fan (17) operate. Operation of the external fan (16) allows outside air outside the shipping container (1) to be sucked into the external equipment room (28) and pass through the condenser (13). In the condenser (13), the refrigerant dissipates heat to the outside air to be condensed. Operation of the internal fan (17) allows inside air in the cargo space (5) of the shipping container (1) to be sucked into the inside air flow path (29) and pass through the evaporator (15). In the evaporator (15), the refrigerant absorbs heat from the inside air to evaporate.

The flow of inside air will be described below. Inside air present in the cargo space (5) flows through the intake port (26) into the primary flow path (29a) of the inside air flow path (29), and is blown to the secondary flow path (29b) by the internal fan (17). The inside air that has flowed into the secondary flow path (29b) is cooled while passing through the evaporator (15). Then, the cooled air is blown through the blowout port (27) to the underfloor path (4), and flows through the underfloor path (4) into the cargo space (5).

The primary flow path (29a) is a portion of the inside air flow path (29) on the suction side of the internal fan (17). The secondary flow path (29b) is a portion of the inside air flow path (29) on the discharge side of the internal fan (17). Thus, during operation of the internal fan (17), the air pressure in the secondary flow path (29b) is slightly higher than the air pressure in the primary flow path (29a).

—Operation of Inside Air Control System—

The inside air control system (30) operates to control the composition of inside air in the cargo space (5) of the shipping container (1) (in this embodiment, the oxygen concentration and carbon dioxide concentration of the inside air). Operation of the inside air control system (30) according to this embodiment will be described with reference to an exemplary situation where the target range of the oxygen concentration of the inside air is 5%±1% and the target range of the carbon dioxide concentration of the inside air is 2%±1%. The target range of the oxygen concentration of the inside air is a numeric range including a target oxygen concentration SP_O2 (in this example, 5%) of the inside air. The target range of the carbon dioxide concentration of the inside air is a numeric range including a target carbon dioxide concentration SP_CO2 (in this example, 2%) of the inside air.

<Outline of Operation of Inside Air Control System>

The inside air control system (30) according to this embodiment performs an oxygen concentration lowering operation for reducing the oxygen concentration of the inside air in the cargo space (5), a carbon dioxide concentration lowering operation for reducing the carbon dioxide concentration of the inside air in the cargo space (5), and an oxygen concentration increasing operation for raising the oxygen concentration of the inside air in the cargo space (5).

The oxygen concentration lowering operation and the oxygen concentration increasing operation correspond to an oxygen control operation for controlling the oxygen concentration of the inside air. The carbon dioxide concentration lowering operation corresponds to a carbon dioxide control operation for controlling the carbon dioxide concentration of the inside air. The carbon dioxide concentration lowering operation serves also as a concentration control operation for controlling the concentration of carbon dioxide as a target gas contained in the inside air.

The composition of the inside air present in the cargo space (5) at the point in time when loading of the shipping container (1) with the cargos (6) is completed is substantially the same as the composition of the atmosphere (nitrogen concentration: 78%, oxygen concentration: 21%, carbon dioxide concentration: 0.04%). To address this situation, the inside air control system (30) performs the oxygen concentration lowering operation for reducing the oxygen concentration of the inside air. If the oxygen concentration of the inside air reaches the upper limit (6%) of the associated target range, the inside air control system (30) stops the oxygen concentration lowering operation.

After the oxygen concentration of the inside air has reached 6%, and the inside air control system (30) has stopped the oxygen concentration lowering operation, breathing of the plants, which are the cargos (6), gradually reduces the oxygen concentration of the inside air, and simultaneously and gradually increases the carbon dioxide concentration of the inside air.

If the carbon dioxide concentration of the inside air reaches the upper limit (3%) of the associated target range, the inside air control system (30) performs the carbon dioxide concentration lowering operation to reduce the carbon dioxide concentration of the inside air. If the carbon dioxide concentration of the inside air reaches the lower limit (1%) of the associated target range, the inside air control system (30) stops the carbon dioxide concentration lowering operation.

If the oxygen concentration of the inside air reaches the lower limit (4%) of the associated target range, the inside air control system (30) performs the oxygen concentration increasing operation to raise the oxygen concentration of the inside air. If the oxygen concentration of the inside air reaches the upper limit (6%) of the associated target range, the inside air control system (30) stops the oxygen concentration increasing operation.

As can be seen, the inside air control system (30) performs the oxygen concentration lowering operation to reduce the oxygen concentration of the inside air in the cargo space (5) from 21% (the oxygen concentration of the atmosphere) to the target range. The inside air control system (30) repeatedly performs the carbon dioxide concentration lowering operation and the oxygen concentration increasing operation as appropriate to maintain the oxygen concentration and carbon dioxide concentration of the inside air in the cargo space (5) within the respective target ranges.

<Oxygen Concentration Lowering Operation>

The oxygen concentration lowering operation of the inside air control system (30) will be described with reference to FIG. 3. In the oxygen concentration lowering operation, the first composition controller (40) supplies the first type of outside air with a low oxygen concentration to the cargo space (5), and the second composition controller (60) supplies the first type of inside air with a low oxygen concentration to the cargo space (5).

In the oxygen concentration lowering operation, the controller (110) makes the first composition controller (40) alternately and repeatedly execute a first operation and a second operation, which will be described below. The operation of the first composition controller (40) will be described below in detail. In the oxygen concentration lowering operation, the controller (110) places the second bypass valve (70) in a first state (the state indicated by the solid line in FIG. 3), energizes the drive motor (38) of the pump unit (35) to actuate the pump body (37), and places the ventilation exhaust valve (101) in the open state.

Operation of the pump body (37) allows inside air present in the shipping container (1) (specifically, the secondary flow path (29b) of the container refrigerator (10)) to be sucked through the internal suction pipe (75) into the pump body (37). The pump body (37) compresses, and discharges, the sucked inside air. The pressure of the inside air discharged by the pump body (37) is of the order slightly higher than the atmospheric pressure. The inside air discharged from the pump body (37) flows, as untreated inside air, through the introduction pipe (72) into the introduction port (62) of the separation module (61).

In the separation module (61), the untreated inside air that has flowed through the introduction port (62) into the introduction chamber (82) flows into the gas separation membranes (85) in the shape of hollow fibers. Part of the air flowing through the interiors of the gas separation membranes (85) permeates the gas separation membranes (85) to move, as the second type of inside air, to the secondary exhaust chamber (84), and the remaining part thereof flows, as the first type of inside air, into the primary exhaust chamber (83). As described above, the nitrogen permeability of the gas separation membranes (85) is lower than the oxygen permeability thereof. Thus, the first type of inside air has a lower oxygen concentration than the untreated inside air, and the second type of inside air has a higher oxygen concentration than the untreated inside air.

The first type of inside air that has flowed out of the primary exhaust port (63) of the separation module (61) into the primary pipe (73) flows into the supply pipe (120). The second type of inside air that has flowed out of the secondary exhaust port (64) of the separation module (61) into the secondary pipe (74) is discharged to the outside of the shipping container (1).

As described above, the first type of outside air that has flowed out of the first separator (41) described below and the first type of inside air that has flowed out of the separation module (61) flow into the supply pipe (120). Then, a mixture of the first type of outside air and the first type of inside air flowing through the supply pipe (120) flows into the secondary flow path (29b) of the container refrigerator (10), and is supplied to the cargo space (5) together with the air flowing through the secondary flow path (29b).

Under normal conditions, during the oxygen concentration lowering operation, the flow rate of the first type of outside air supplied from the outside to the inside of the shipping container (1) is higher than the flow rate of the second type of inside air discharged from the inside to the outside of the shipping container (1), and the air pressure inside the shipping container (1) is thus positive. Since the air pressure inside the shipping container (1) is positive, part of the inside air is discharged through the ventilation exhaust pipe (100) to the outside of the shipping container (1).

As can be seen, in the oxygen concentration lowering operation, while the first type of outside air with a lower oxygen concentration than the atmosphere is supplied into the shipping container (1), the inside air in the cargo space (5) is discharged through the ventilation exhaust pipe (100) to the outside of the shipping container (1) so as to be replaced with the first type of outside air. This reduces the oxygen concentration of the inside air in the cargo space (5). In the oxygen concentration lowering operation, the second type of inside air separated from the untreated inside air and having a high oxygen concentration is discharged to the outside of the shipping container (1) to reduce the oxygen concentration of the inside air in the cargo space (5).

<Carbon Dioxide Concentration Lowering Operation>

The carbon dioxide concentration lowering operation of the inside air control system (30) will be described with reference to FIG. 3. In the carbon dioxide concentration lowering operation, each of the first and second composition controllers (40) and (60) performs an operation similar to the oxygen concentration lowering operation. In the carbon dioxide concentration lowering operation, the first composition controller (40) supplies the first type of outside air with a low oxygen concentration to the cargo space (5), and the second composition controller (60) supplies the first type of inside air with a low carbon dioxide concentration to the cargo space (5).

The first composition controller (40) separates untreated outside air that has flowed into the first separator (41) described below into the first type of outside air having a higher nitrogen concentration and a lower oxygen concentration than the untreated outside air, and the second type of outside air having a lower nitrogen concentration and a higher oxygen concentration than the untreated outside air. Then, the first type of outside air is supplied into the shipping container (1), and the second type of outside air is discharged to the outside of the shipping container (1). The carbon dioxide concentration of the untreated outside air is substantially the same as the carbon dioxide concentration (0.04%) of the atmosphere. Thus, the carbon dioxide concentration of the first type of outside air can be assumed to be substantially zero.

The second composition controller (60) separates untreated inside air that has flowed into the separation module (61) into the first type of inside air having a higher nitrogen concentration, a lower oxygen concentration, and a lower carbon dioxide concentration than the untreated inside air, and the second type of inside air having a lower nitrogen concentration, a higher oxygen concentration, and a higher carbon dioxide concentration than the untreated inside air. Then, the first type of inside air is supplied into the shipping container (1), and the second type of inside air is discharged to the outside of the shipping container (1).

Under normal conditions, during the carbon dioxide concentration lowering operation, just like the oxygen concentration lowering operation, the flow rate of the first type of outside air is higher than the flow rate of the second type of inside air, and the air pressure inside the shipping container (1) is thus positive. Since the air pressure inside the shipping container (1) is positive, part of the inside air in the cargo space (5) is discharged through the ventilation exhaust pipe (100) to the outside of the shipping container (1).

As can be seen, in the carbon dioxide concentration lowering operation, while the first type of outside air with an extremely low carbon dioxide concentration is supplied into the shipping container (1), the inside air in the cargo space (5) is discharged through the ventilation exhaust pipe (100) to the outside of the shipping container (1) so as to be replaced with the first type of outside air. This reduces the carbon dioxide concentration of the inside air in the cargo space (5). In the carbon dioxide concentration lowering operation, the second type of inside air separated from the untreated inside air and having a high carbon dioxide concentration is discharged to the outside of the shipping container (1) to reduce the carbon dioxide concentration of the inside air in the cargo space (5).

<Oxygen Concentration Increasing Operation>

Figure 6:
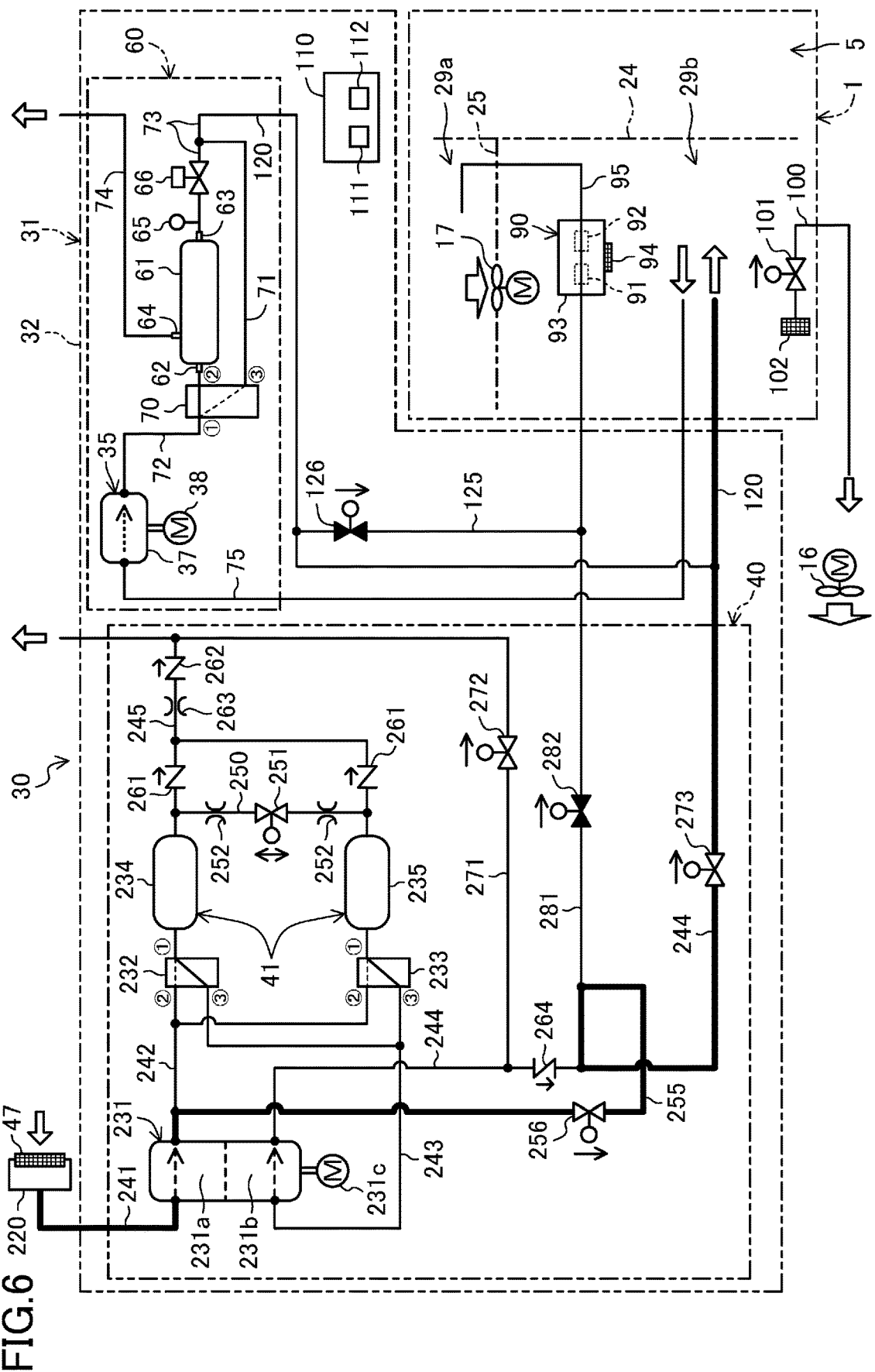
FIG. 6 is a piping system diagram of an inside air control system showing a state of the inside air control system that is performing an oxygen concentration increasing operation according to an embodiment.

The oxygen concentration increasing operation of the inside air control system (30) will be described with reference to FIG. 6. In the oxygen concentration increasing operation, the first composition controller (40) supplies outside air sucked from the outside of the shipping container (1) directly to the cargo space (5), and the second composition controller (60) pauses.

In the oxygen concentration increasing operation, the controller (110) places each of the first and second directional control valves (232) and (233) in a second state (the state indicated by the solid line in FIG. 6), and energizes the motor (231c) of the air pump (231) to actuate the first pump mechanism (231a). The controller (110) places the first bypass valve (256), the exhaust on-off valve (272), and the supply on-off valve (273) in their open states, and places the measurement on-off valves (126, 282) in their closed states. The drive motor (38) of the pump unit (35) is not energized.

Outside air discharged from the first pump mechanism (231a) of the first composition controller (40) flows through the first bypass pipe (255) and the supply connection pipe (244) in this order, and is then supplied through the supply pipe (120) into the shipping container (1). Part of the inside air in the cargo space (5) is discharged through the ventilation exhaust pipe (100) to the outside of the shipping container (1).

Energizing the motor (231c) of the air pump (231) allows not only the first pump mechanism (231a) but also the second pump mechanism (231b) to operate. The second pump mechanism (231b) sucks gas (components of air remaining in the first and second adsorption columns (234) and (235)) from the first and second adsorption columns (234) and (235), and discharges the sucked gas. The gas discharged by the second pump mechanism (231b) is discharged through the exhaust connection pipe (271) to the outside of the shipping container (1).

As can be seen, in the oxygen concentration increasing operation, the outside air having a higher oxygen concentration than the inside air is supplied into the shipping container (1) to increase the oxygen concentration of the air in the cargo space (5).

—Operation of First Composition Controller—

Operation of the first composition controller (40) will be described.

The first composition controller (40) alternately and repeatedly performs first and second operations described below for a predetermined period of time (e.g., 14.5 seconds) to separate the untreated outside air into the first type of outside air and the second type of outside air. The first composition controller (40) performs an operation for separating the untreated outside air into the first type of outside air and the second type of outside air in each of the oxygen concentration lowering operation and the carbon dioxide concentration lowering operation of the inside air control system (30).

The first composition controller (40) is capable of executing an outdoor air supply operation, which will be described below. The outdoor air supply operation is an operation for supplying outside air sucked from the outside of the shipping container (1) directly to the sensor unit (90).

<First Operation>

Figure 7:
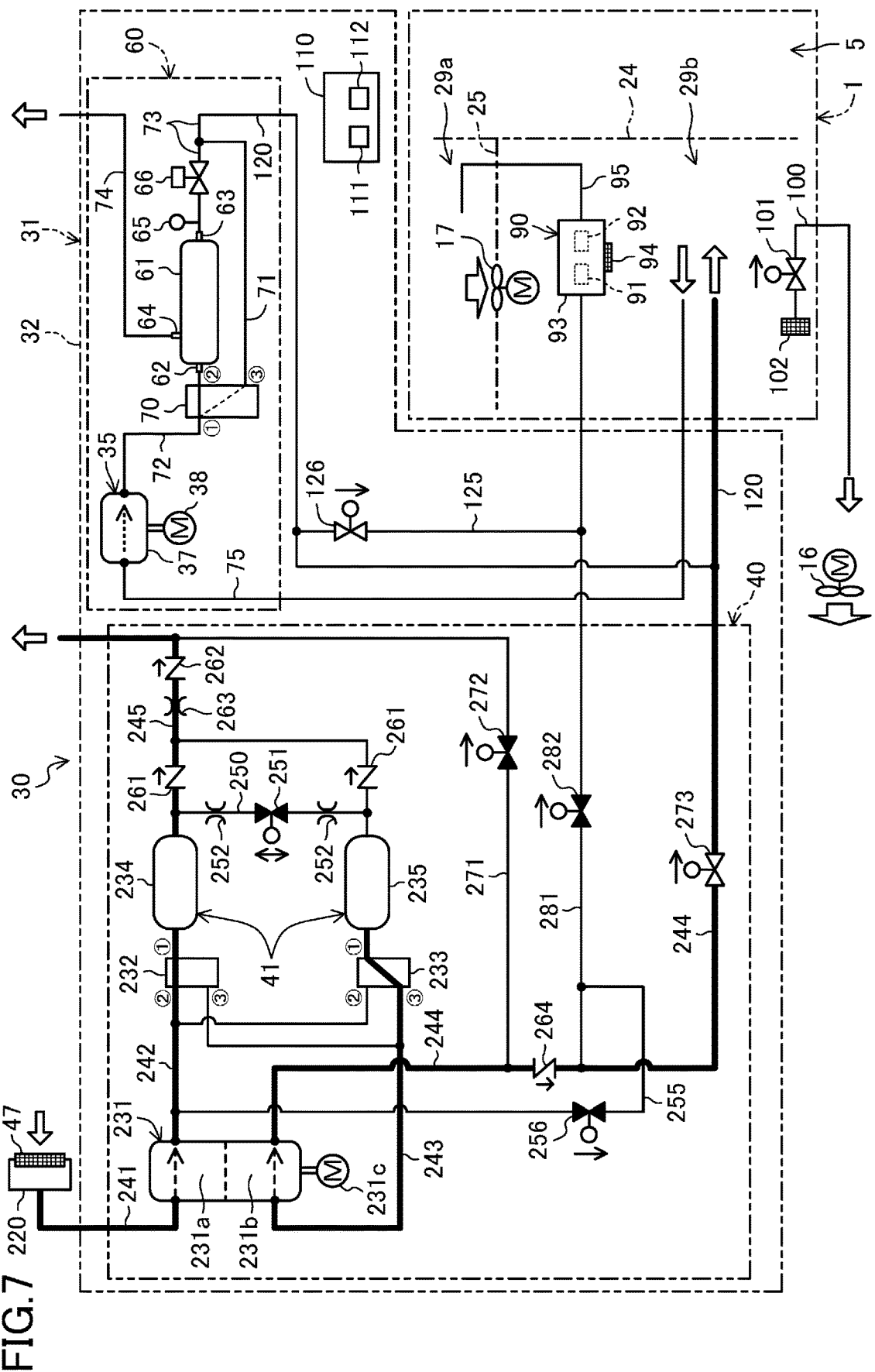
FIG. 7 is a piping system diagram of an inside air control system showing a state of a first composition controller that is performing a first operation according to an embodiment.

As illustrated in FIG. 7, in the first operation, the first directional control valve (232) is placed in the first state, and the second directional control valve (233) is placed in the second state. As a result, the blowout port of the first pump mechanism (231a) is connected to the first adsorption column (234), and the second adsorption column (235) is connected to the intake port of the second pump mechanism (231b). In the first operation, the supply on-off valve (273) is opened, and the remaining on-off valves (251, 256, 272, 282) are closed. In the first operation, an adsorption operation for the first adsorption column (234) and a desorption operation for the second adsorption column (235) are performed.

The first pump mechanism (231a) sucks untreated outside air from the outdoor air pipe (241), compresses the sucked untreated outside air, and supplies the compressed untreated outside air to the first adsorption column (234). Nitrogen contained in the untreated outside air supplied to the first adsorption column (234) is adsorbed on the adsorbent. As a result, the first adsorption column (234) produces the second type of outside air having a lower nitrogen concentration and a higher oxygen concentration than the untreated outside air. The second type of outside air flows out of the first adsorption column (234), flows through the oxygen discharge pipe (245), and is discharged, as discharge air, to a space outside the shipping container (1).

In contrast, the second pump mechanism (231b) sucks the air from the second adsorption column (235). The second adsorption column (235) has its internal pressure reduced, and nitrogen is thus desorbed from the adsorbent. As a result, the second adsorption column (235) produces the first type of outside air having a higher nitrogen concentration and a lower oxygen concentration than the untreated outside air. The first type of outside air flows from the second adsorption column (235) into the suction pipe (243), and is sucked into the second pump mechanism (231b). The second pump mechanism (231b) compresses the sucked first type of outside air, and discharges the compressed air to the supply connection pipe (244). The first type of outside air flows, as supply air, through the supply connection pipe (244), and is supplied into the internal space of the shipping container (1) after merging with the air flowing through the supply pipe (120).

<Second Operation>

Figure 8:
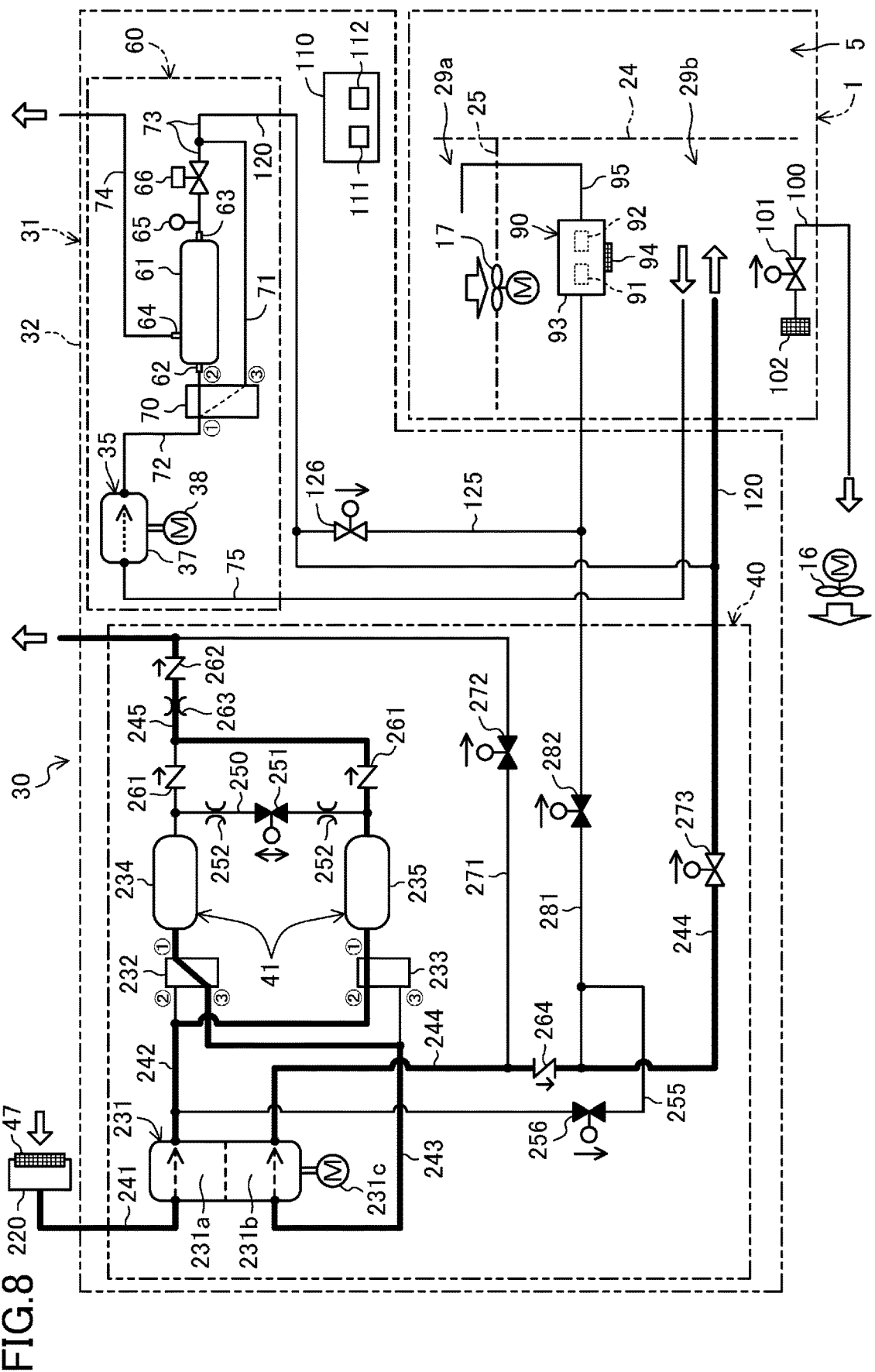
FIG. 8 is a piping system diagram of an inside air control system showing a state of a first composition controller that is performing a second operation according to an embodiment.

As illustrated in FIG. 8, in the second operation, the first directional control valve (232) is placed in the second state, and the second directional control valve (233) is placed in the first state. As a result, the blowout port of the first pump mechanism (231a) is connected to the second adsorption column (235), and the first adsorption column (234) is connected to the intake port of the second pump mechanism (231b). In the second operation, the supply on-off valve (273) is opened, and the remaining on-off valves (251, 256, 272, 282) are closed. In the second operation, a desorption operation for the first adsorption column (234) and an adsorption operation for the second adsorption column (235) are performed.

The first pump mechanism (231a) sucks untreated outside air from the outdoor air pipe (241), compresses the sucked untreated outside air, and supplies the compressed untreated outside air to the second adsorption column (235). Nitrogen contained in the untreated outside air supplied to the second adsorption column (235) is adsorbed on the adsorbent. As a result, the second adsorption column (235) produces the second type of outside air having a lower nitrogen concentration and a higher oxygen concentration than the untreated outside air. The second type of outside air flows out of the second adsorption column (235), flows through the oxygen discharge pipe (245), and is discharged, as discharge air, to a space outside the shipping container (1).

In contrast, the second pump mechanism (231b) sucks the air from the first adsorption column (234). The first adsorption column (234) has its internal pressure reduced, and nitrogen is thus desorbed from the adsorbent. As a result, the first adsorption column (234) produces the first type of outside air having a higher nitrogen concentration and a lower oxygen concentration than the untreated outside air.

The first type of outside air flows from the first adsorption column (234) into the suction pipe (243), and is sucked into the second pump mechanism (231b). The second pump mechanism (231b) compresses the sucked first type of outside air, and discharges the compressed air to the supply connection pipe (244). The first type of outside air flows, as supply air, through the supply connection pipe (244), and is supplied into the internal space of the shipping container (1) after merging with the air flowing through the supply pipe (120).

<Outdoor Air Supply Operation>

Figure 9:
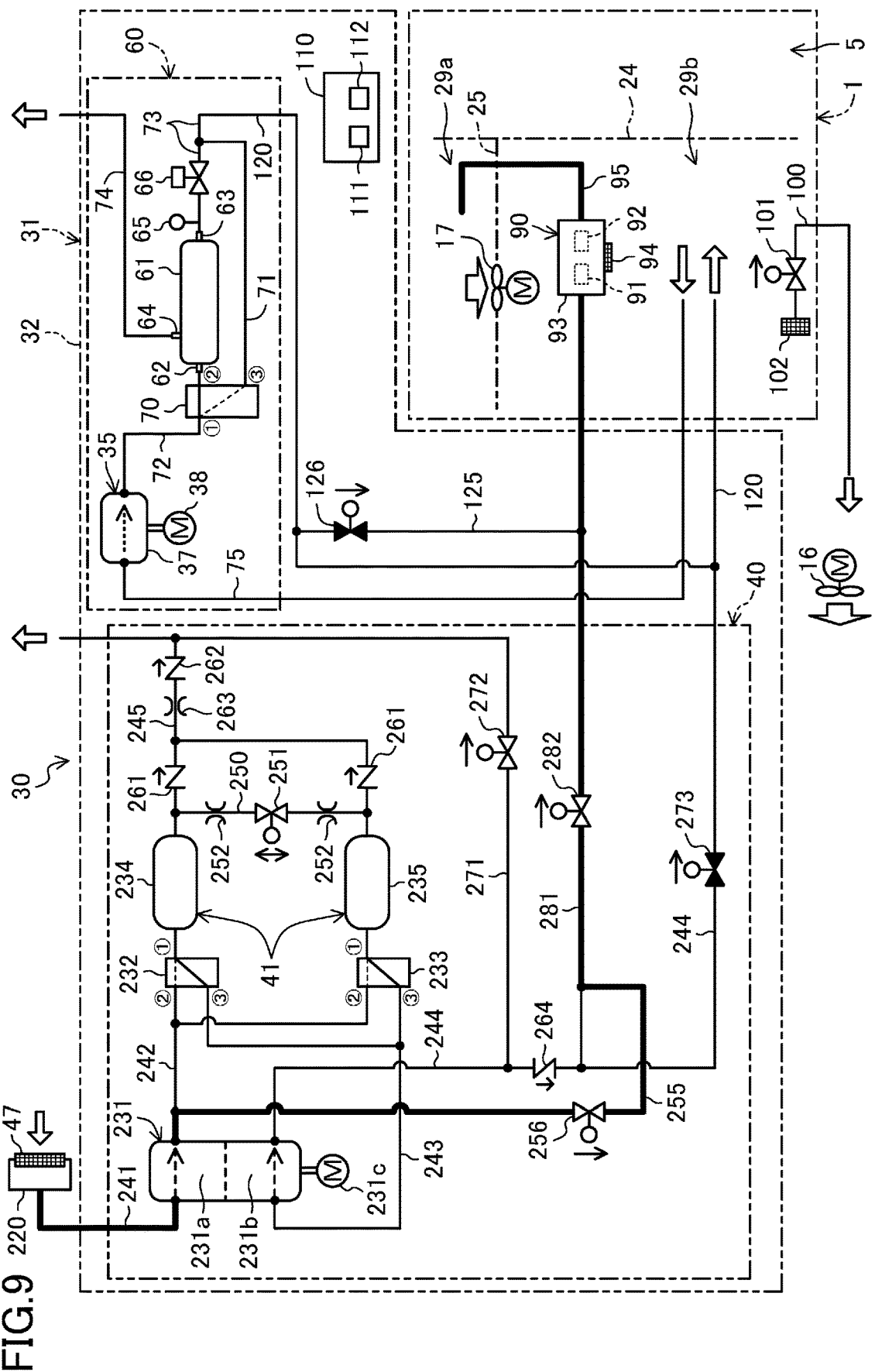
FIG. 9 is a piping system diagram of an inside air control system showing a state of a first composition controller that is performing an outdoor air supply operation according to an embodiment.

As illustrated in FIG. 9, in the outdoor air supply operation, the controller (110) places each of the first and second directional control valves (232) and (233) in a second state (the state indicated by the solid line in FIG. 9), and energizes the motor (231c) of the air pump (231) to actuate the first pump mechanism (231a). The controller (110) places the first bypass valve (256), the exhaust on-off valve (272), the first measurement on-off valve (282), and the purge valve (251) in their open states, and places the supply on-off valve (273) and the measurement on-off valve (126) of the second composition controller (60) in their closed states. Just like the oxygen concentration increasing operation, the second composition controller (60) pauses.

In the outdoor air supply operation, the outside air discharged from the first pump mechanism (231a) flows through the first bypass pipe (255) and the measurement connection pipe (281) in this order into the sensor unit (90). In the sensor unit (90), the outside air flows through the sensor case (93) housing the oxygen sensor (91) and the carbon dioxide sensor (92). The outside air that has flowed out of the sensor case (93) of the sensor unit (90) flows through the blowout port pipe (95) into the shipping container (1). The flow of gas through the second pump mechanism (231b) is the same as that in the oxygen concentration increasing operation.

—Operation of Controller—

Operation performed by the controller (110) will be described.

<Air Composition Control Operation>

The air composition control unit (115) of the controller (110) performs the air composition control operation. The air composition control operation is an operation for controlling the operation of the inside air control system (30) so that the oxygen concentration and carbon dioxide concentration of the inside air fall within their respective target ranges. In principle, the air composition control unit (115) performs the air composition control operation whenever the inside air control system (30) is in operation. As a result of the air composition control operation performed by the air composition control unit (115), the inside air control system (30) performs the operation described in the foregoing section "Outline of Operation of Inside Air Control System."

Specifically, the air composition control unit (115) monitors the measured values respectively obtained by the oxygen sensor (91) and the carbon dioxide sensor (92). If the value measured by the oxygen sensor (91) falls outside the target range of the oxygen concentration, the inside air control system (30) is instructed to execute the oxygen concentration lowering operation or the oxygen concentration increasing operation so that the measured value obtained by the oxygen sensor (91) falls within the target range of the oxygen concentration. If the value measured by the carbon dioxide sensor (92) falls outside the target range of the carbon dioxide concentration, the inside air control system (30) is instructed to execute the carbon dioxide concentration lowering operation so that the measured value obtained by the carbon dioxide sensor (92) falls within the target range of the carbon dioxide concentration.

<Calibration Operation>

The sensor calibrator (116) of the controller (110) performs the calibration operation. The calibration operation is an operation for calibrating the carbon dioxide sensor (92) using outside air (outdoor air).

The sensor calibrator (116) performs the calibration operation during pre-trip inspection (PTI) of the container refrigerator (10). The sensor calibrator (116) also performs the calibration operation every time a predetermined period (e.g., 7 days) passes during transportation of the cargos (6) using the shipping container (1).

In the calibration operation, the sensor calibrator (116) instructs the inside air control system (30) to perform the outdoor air supply operation. In the outdoor air supply operation, the outside air (outdoor air) sucked into the first pump mechanism (231a) is supplied to the sensor unit (90) without controlling its composition (see FIG. 9). In other words, in the outdoor air supply operation, the atmosphere is supplied to the sensor unit (90).

In the calibration operation, the lapse of a predetermined period of time (e.g., 10 minutes) since the inside air control system (30) starts the outdoor air supply operation allows the sensor calibrator (116) to acquire the measured value obtained by the carbon dioxide sensor (92). If the duration of the state where the atmosphere flows through the sensor case (93) of the sensor unit (90) exceeds a predetermined period of time, a target that has its carbon dioxide concentration measured by the carbon dioxide sensor (92) in the sensor case (93) can be assumed to be substantially "the atmosphere." The carbon dioxide concentration of the atmosphere is a known value (0.04%).

Thus, the sensor calibrator (116) corrects the value measured by the carbon dioxide sensor (92) so that the measured value obtained by the carbon dioxide sensor (92) and acquired upon the lapse of a predetermined period of time since the start of the outdoor air supply operation is equal to "zero." That is to say, the sensor calibrator (116) calibrates the carbon dioxide sensor (92) based on the carbon dioxide concentration of the atmosphere.

<Sensor Abnormality Handling Operation>

The sensor abnormality handler (117) of the controller (110) performs the sensor abnormality handling operation. The sensor abnormality handling operation is an operation for handling the situation where the measured value obtained by the carbon dioxide sensor (92) is abnormal.

Here, the carbon dioxide sensor (92) may fail to output the correct carbon dioxide concentration. For example, the carbon dioxide sensor (92) outputting an abnormal measured value due to breakage of the carbon dioxide sensor (92) or any other factor needs repair such as replacement of the carbon dioxide sensor (92).

However, even if the structure itself of the carbon dioxide sensor (92) has no problem, the carbon dioxide sensor (92) on which condensation occurs, for example, may output an abnormal measured value. In this case, evaporation of condensed water after a lapse of a certain period of time allows the carbon dioxide sensor (92) to again output the correct measured value without repair such as replacement of the carbon dioxide sensor (92).

Thus, if the carbon dioxide sensor (92) outputs an abnormal measured value, the sensor abnormality handler (117) determines whether or not the carbon dioxide sensor (92) is normal, and performs an operation corresponding to the determination result.

For reference, a phenomenon caused by condensation on the carbon dioxide sensor (92) will be described. As described above, the carbon dioxide sensor (92) according to this embodiment is an NDIR sensor. A gas (target gas) that has its carbon dioxide concentration measured flows through a portion of the carbon dioxide sensor (92) between a light source and a light receiving element. The target gas with high humidity may cause condensation on the surface of the light source. The condensation on the surface of the light source causes light emitted from the light source to be scattered by water droplets, and thus reduces the amount of light reaching the light receiving element. This causes the measured value obtained by the carbon dioxide sensor (92) to be drastically different from the actual carbon dioxide concentration of the target gas.

Figure 10:
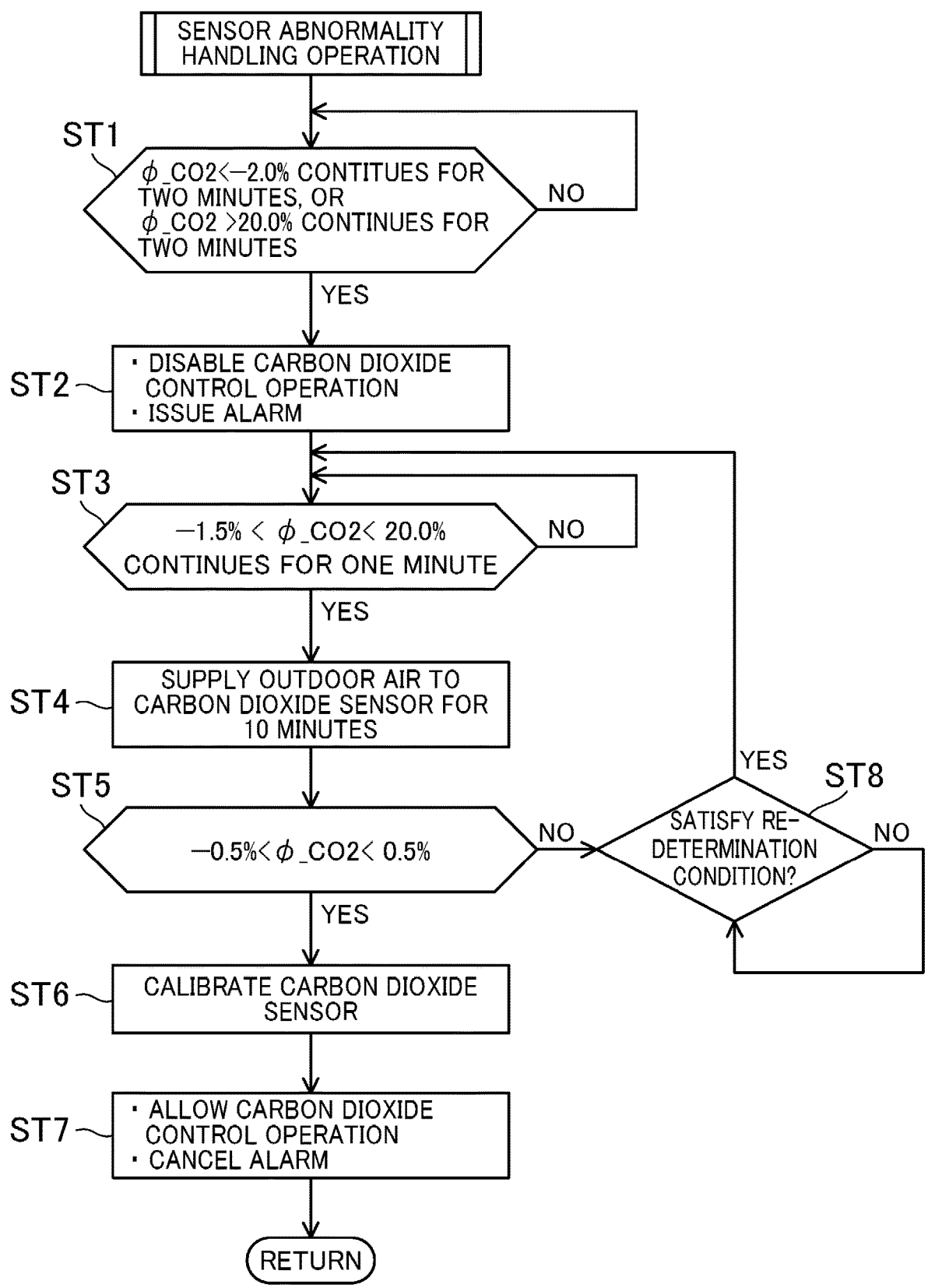
FIG. 10 is a flowchart showing a sensor abnormality handling operation performed by a controller of an inside air control system according to an embodiment.

The sensor abnormality handling operation performed by the sensor abnormality handler (117) will be described with reference to the flowchart of FIG. 10. Note that the period of time and measured value obtained by the carbon dioxide sensor (92) which are used in the following description are merely examples.

During the operation of the inside air control system (30), the sensor abnormality handler (117) acquires the measured value obtained by the carbon dioxide sensor (92) at predetermined time intervals (e.g., every several tens of seconds).

[Step ST1]

In step ST1, the sensor abnormality handler (117) determines whether or not a first or second condition has been satisfied. The first condition is a condition where "the state in which the measured value $\varphi\_CO2$ obtained by the carbon dioxide sensor (92) is below −2.0% ($\varphi\_CO2<-2.0\%$) continues for two minutes." The second condition is a condition where "the state in which the measured value $\varphi\_CO2$ obtained by the carbon dioxide sensor (92) is above 20.0% ($\varphi\_CO2>20.0\%$) continues for two minutes."

Here, the carbon dioxide concentration of a mixed gas, such as air, cannot actually be a negative value. The upper limit of the range measurable by the carbon dioxide sensor (92) according to this embodiment is 20.0%. Thus, each of the first and second conditions is a condition indicating that the state in which the measured value output by the carbon dioxide sensor (92) is outside the normal range continues for a period of time longer than or equal to a predetermined period of time (in this embodiment, two minutes).

If neither the first nor second condition is satisfied in step ST1, the sensor abnormality handler (117) continues to monitor the measured value obtained by the carbon dioxide sensor (92). On the other hand, if either the first or second condition is satisfied, the sensor abnormality handler (117) allows the process to proceed to step ST2.

[Step ST2]

In step ST2, the sensor abnormality handler (117) disables the carbon dioxide concentration lowering operation of the inside air control system (30). If either the first or second condition is satisfied, the measured value obtained by the carbon dioxide sensor (92) can be estimated to be different from the actual carbon dioxide concentration of the inside air. Thus, in this case, the sensor abnormality handler (117) disables the carbon dioxide concentration lowering operation. Even if the measured value obtained by the carbon dioxide sensor (92) falls outside the target carbon dioxide concentration range while the sensor abnormality handler (117) disables the carbon dioxide concentration lowering operation, the air composition control unit (115) prevents the inside air control system (30) from executing the carbon dioxide concentration lowering operation.

In contrast, in this step ST2, the oxygen concentration lowering operation and the oxygen concentration increasing operation of the inside air control system (30) are not disabled. Thus, even after the sensor abnormality handler (117) has disabled the carbon dioxide concentration lowering operation, the air composition control unit (115) continues to perform an operation for controlling the oxygen concentration of the inside air based on the measured value obtained by the oxygen sensor (91). Specifically, if the value measured by the oxygen sensor (91) falls outside the target range of the oxygen concentration, the air composition control unit (115) instructs the inside air control system (30) to execute the oxygen concentration lowering operation or the oxygen concentration increasing operation so that the measured value obtained by the oxygen sensor (91) falls within the target range.

In step ST2, the sensor abnormality handler (117) issues an alarm indicating that an abnormality has occurred in the carbon dioxide sensor (92). The alarm is issued to notify an operator who manages and maintains the container refrigerator (10) of an abnormality in the carbon dioxide sensor (92). Examples of the alarm include illumination of a warning light provided on an operating section of the container refrigerator (10), and a warning displayed on a liquid crystal display screen provided on the operating section.

[Step ST3]

In the next step ST3, the sensor abnormality handler (117) determines whether or not a third condition has been satisfied. The third condition is a condition where "the state in which the measured value $\varphi\_CO2$ obtained by the carbon dioxide sensor (92) is above −1.5% and below 20.0% ($-1.5\%<\varphi\_CO2<20.0\%$) continues for one minute." The third condition is a condition indicating that the measured value obtained by the carbon dioxide sensor (92) falls within the normal range.

For example, if condensation on the carbon dioxide sensor (92) causes the measured value obtained by the carbon dioxide sensor (92) to fall outside the normal range, the lapse of a certain period of time reduces the amount of water droplets that have adhered to the carbon dioxide sensor (92), and the value measured by the carbon dioxide sensor (92) thus returns to the normal range. If the measured value obtained by the carbon dioxide sensor (92) returns to the normal range after falling outside the normal range, the carbon dioxide sensor (92) itself is highly likely not to be damaged.

Thus, if the third condition is satisfied in step ST3, the sensor abnormality handler (117) determines that the carbon dioxide sensor (92) may continue to be used, and the process proceeds to step ST4. On the other hand, if the third condition is not satisfied in step ST3, the carbon dioxide sensor (92) is highly likely to be damaged. Thus, in this case, the sensor abnormality handler (117) continues the disabling of the carbon dioxide concentration lowering operation and the issue of the alarm both executed in step ST2, and also continues to monitor the measured value obtained by the carbon dioxide sensor (92).

[Step ST4]

In step ST4, the sensor abnormality handler (117) instructs the inside air control system (30) to execute the outdoor air supply operation. In this outdoor air supply operation, outside air (outdoor air) is supplied to the sensor unit (90). If the duration of the outdoor air supply operation reaches a certain period of time, the composition of the air in the sensor case (93) of the sensor unit (90) is substantially the same as that of outside air. Thus, the carbon dioxide sensor (92) can be estimated to have become ready to measure the carbon dioxide concentration of outside air. Thus, the sensor abnormality handler (117) continues the outdoor air supply operation for a predetermined period of time (in this embodiment, 10 minutes). If the duration of the outdoor air supply operation reaches 10 minutes, the process proceeds to the next step ST5.

[Step ST5]

In step ST5, the sensor abnormality handler (117) instructs the sensor determiner (118) to execute the determination operation. This determination operation is an operation for using outside air (outdoor air) to determine whether or not the carbon dioxide sensor (92) is normal.

Specifically, in step ST5, the sensor determiner (118) determines whether or not a fourth condition has been satisfied. The fourth condition is a condition where "the measured value $\varphi\_CO2$ obtained by the carbon dioxide sensor (92) is above −0.5% and below 0.5% (−0.5%<$\varphi\_CO2$<0.5%)." The range "−0.5%<$\varphi\_CO2$<0.5%" is a reference range including the carbon dioxide concentration (0.04%) of the atmosphere.

The carbon dioxide concentration of outside air is equal to the carbon dioxide concentration (0.04%) of the atmosphere. Thus, if the measured value $\varphi\_CO2$ obtained by the carbon dioxide sensor (92) satisfies the condition "−0.5%<$\varphi\_CO2$<0.5%," a determination can be made that the carbon dioxide sensor (92) has functioned normally.

If the fourth condition is satisfied in step ST5, and the sensor determiner (118) determines that the carbon dioxide sensor (92) has functioned normally, the sensor abnormality handler (117) allows the process to proceed to step ST6. On the other hand, if the fourth condition is not satisfied in step ST5, and the sensor determiner (118) determines that the carbon dioxide sensor (92) has not functioned normally, the sensor abnormality handler (117) allows the process to proceed to step ST8.

[Step ST6]

As described above, if the fourth condition is satisfied in step ST5, the sensor determiner (118) determines that the carbon dioxide sensor (92) is normal. In this case, the sensor abnormality handler (117) instructs the sensor calibrator (116) to execute the calibration operation in step ST6. However, outside air has already been supplied to the sensor unit (90) for 10 minutes or longer until the sensor abnormality handler (117) executes the operation of step ST6. Thus, in step ST6, the sensor calibrator (116) immediately acquires the measured value obtained by the carbon dioxide sensor (92), and corrects the value measured by the carbon dioxide sensor (92) so that the value measured by the carbon dioxide sensor (92) at the moment is equal to "zero." If the operation of step ST6 is completed, the sensor abnormality handler (117) allows the process to proceed to step ST7.

[Step ST7]

At the end of step ST6, the carbon dioxide sensor (92) has been determined to have functioned normally, and calibration of the carbon dioxide sensor (92) has been completed. Thus, in step ST7, the sensor abnormality handler (117) allows the carbon dioxide concentration lowering operation of the inside air control system (30) disabled in step ST2. If the measured value obtained by the carbon dioxide sensor (92) falls outside the target range of the carbon dioxide concentration while the sensor abnormality handler (117) allows the carbon dioxide lowering operation, the air composition control unit (115) instructs the inside air control system (30) to execute the carbon dioxide concentration lowering operation. The sensor abnormality handler (117) cancels the alarm issued in step ST2. Completion of the operation of step ST7 allows the sensor abnormality handler (117) to terminate the sensor abnormality handling operation.

[Step ST8]

As described above, if the fourth condition is not satisfied in step ST5, the sensor determiner (118) determines that the carbon dioxide sensor (92) is not normal. In this case, the sensor abnormality handler (117) allows the process to proceed to step ST8, and determines whether or not a re-determination condition has been satisfied. When allowing the process to proceed to step ST8, the sensor abnormality handler (117) instructs the inside air control system (30) to stop the outdoor air supply operation.

If the re-determination condition is not satisfied, the sensor abnormality handler (117) allows the process to remain in step ST8. While the process remains in step ST8, the sensor abnormality handler (117) disables the carbon dioxide concentration lowering operation of the inside air control system (30), and maintains the issued alarm. On the other hand, if the re-determination condition is satisfied, the sensor abnormality handler (117) allows the process to return to step ST3, and again determines whether or not the measured value obtained by the carbon dioxide sensor (92) has been within the normal range.

The re-determination condition is a condition where "a time condition or an oxygen concentration condition is satisfied." The time condition is a condition where "a predetermined period of time (in this embodiment, 24 hours) has elapsed since the sensor abnormality handler (117) allows the process to proceed from step ST5 to step ST8 to stop the outdoor air supply operation of the inside air control system (30)." The oxygen concentration condition is a condition where "the measured value $\varphi\_O2$ obtained by the oxygen sensor (91) falls within a predetermined range (in this embodiment, a target oxygen concentration $SP\_O2$ of inside air±0.5%)." That is to say, the oxygen concentration condition is a condition where the relationship "$SP\_O2 − 0.5\% \leq \varphi\_O2 \leq SP\_O2 + 0.5\%$" is satisfied.

The reason why the condition where "the time condition or the oxygen concentration condition is satisfied" is used as the re-determination condition will be described.

Some of the causes why the measured value obtained by the carbon dioxide sensor (92) falls outside the predetermined normal range are eliminated after a lapse of a certain period of time. Thus, even if the sensor determiner (118) determines in the determination operation that the carbon dioxide sensor (92) is not normal, the determination operation again performed later may allow a determination to be made that the carbon dioxide sensor (92) is normal.

The determination operation of the sensor determiner (118) requires supply of the atmosphere to the sensor unit (90). The inside air control system (30) according to this embodiment allows the atmosphere supplied to the sensor unit (90) to flow through the blowout port pipe (95) into the internal space of the shipping container (1). Thus, the atmosphere supplied to the sensor unit (90) increases the oxygen concentration of inside air. If the oxygen concentration of inside air is close to the target oxygen concentration $SP\_O2$, the difference between the oxygen concentration of inside air and the target oxygen concentration $SP\_O2$ does not increase much, although the atmosphere supplied to the sensor unit (90) increases the oxygen concentration of inside air to a certain degree.

Thus, if the time condition where "24 hours have elapsed since the sensor abnormality handler (117) stops the outdoor air supply operation of the inside air control system (30)" or the oxygen concentration condition where "the measured value φ_O2 obtained by the oxygen sensor (91) falls within the range SP_O2±0.5%" is satisfied, the sensor abnormality handler (117) allows the process to return to step ST3, and again determines whether or not the value measured by the carbon dioxide sensor (92) has been within the normal range.

—Feature (1) of Embodiment—

The inside air control system (30) according to this embodiment includes a gas sensor (92) that measures the concentration of a target gas (in this embodiment, carbon dioxide) contained in inside air in the shipping container (1), and performs the concentration control operation to control the concentration of the target gas in the inside air based on a measured value obtained by the gas sensor (92). This inside air control system (30) includes the outdoor air supply passage (255, 281) through which outdoor air is to be supplied to the gas sensor (92), and the controller (110). If the measured value obtained by the gas sensor (92) returns to a predetermined normal range after falling outside the normal range, the controller (110) performs the determination operation. This determination operation is an operation for supplying outdoor air through the outdoor air supply passage (255, 281) to the gas sensor (92) to determine whether or not the gas sensor (92) is normal.

If the measured value obtained by the gas sensor (92) returns to the normal range after falling outside the normal range, the controller (110) of the inside air control system (30) according to this embodiment performs the determination operation. If the measured value obtained by the gas sensor (92) falls outside the normal range, and later returns to the normal range, the gas sensor (92) may be able to function normally. Thus, in this case, the controller (110) performs the determination operation to determine whether or not the gas sensor (92) is normal. In the determination operation, outdoor air is supplied through the outdoor air supply passage (255, 281) to the gas sensor (92). The concentration of the target gas in the outdoor air is usually known. Thus, if the measured value obtained by the gas sensor (92) to which outdoor air has been supplied is grasped, a determination can be made whether or not the gas sensor (92) is normal, based on the grasped value.

If the controller (110) of the inside air control system (30) according to this embodiment determines in the determination operation that the gas sensor (92) is normal, the gas sensor (92) can continue to be used without being replaced. Thus, according to this embodiment, a determination can be made whether or not, if the measured value obtained by the gas sensor (92) temporarily falls outside the normal range, the gas sensor (92) can continue to be used. This can avoid unneeded repair of the gas sensor (92) to reduce the running cost of the inside air control system (30).

—Feature (2) of Embodiment—

If the measured value obtained by the gas sensor (92) falls within a predetermined reference range including the concentration of a target gas in outdoor air that is being supplied to the gas sensor (92), the controller (110) of the inside air control system (30) according to this embodiment determines in the determination operation that the gas sensor (92) is normal. If the measured value obtained by the gas sensor (92) falls outside the reference range, the controller (110) determines that the gas sensor (92) is not normal.

The controller (110) according to this embodiment compares the measured value obtained by the gas sensor (92) to which outdoor air is being supplied with the predetermined reference range to determine whether or not the gas sensor (92) is normal.

—Feature (3) of Embodiment—

If the controller (110) of the inside air control system (30) according to this embodiment determines in the determination operation that the gas sensor (92) is normal, the controller (110) calibrates the gas sensor (92) based on the measured value obtained by the gas sensor (92) to which outdoor air is being supplied.

If the controller (110) according to this embodiment determines in the determination operation that the gas sensor (92) is normal, the controller (110) calibrates the gas sensor (92). The controller (110) calibrates the gas sensor (92) based on the measured value obtained by the gas sensor (92) to which outdoor air is being supplied.

—Feature (4) of Embodiment—

If the measured value obtained by the gas sensor (92) falls outside the predetermined normal range, the controller (110) of the inside air control system (30) according to this embodiment stops the concentration control operation (in this embodiment, the carbon dioxide concentration lowering operation). If the measured value obtained by the gas sensor (92) falls outside the predetermined normal range, the controller (110) according to this embodiment stops the concentration control operation of the inside air control system (30). This can avoid the concentration control operation based on an incorrect measured value obtained by the gas sensor (92).

—Feature (5) of Embodiment—

If the controller (110) of the inside air control system (30) according to this embodiment determines in the determination operation that the gas sensor (92) is not normal, the controller (110) temporarily stops supply of outdoor air to the gas sensor (92). If a predetermined re-determination condition is thereafter satisfied, the controller (110) again performs the determination operation.

If the controller (110) of the inside air control system (30) according to this embodiment determines in the determination operation that the gas sensor (92) is not normal, the controller (110) temporarily stops supply of outdoor air to the gas sensor (92). If the re-determination condition is thereafter satisfied, the controller (110) again performs the determination operation. As described above, some of the causes why the measured value obtained by the gas sensor (92) falls outside the predetermined normal range are eliminated after a lapse of a certain period of time. Thus, even if the controller (110) determines in the determination operation that the gas sensor (92) is not normal, the determination operation again performed later may allow a determination to be made that the gas sensor (92) is normal. Thus, according to this embodiment, the determination operation again performed can reduce the risk of incorrectly determining the normal gas sensor (92) to be an abnormal one.

—Feature (6) of Embodiment—

The inside air control system (30) according to this embodiment includes the oxygen sensor (91) that measures the concentration of oxygen contained in inside air, and performs the oxygen control operation to control the concentration of oxygen in the inside air based on the measured value obtained by the oxygen sensor (91). The re-determination condition for the controller (110) according to this embodiment is a condition where "a predetermined period of time has elapsed since the supply of outdoor air to the gas sensor (92) is temporarily stopped, or the measured value obtained by the oxygen sensor (91) falls within a predetermined range."

The inside air control system (30) according to this embodiment includes the oxygen sensor (91), and performs the oxygen control operation. If the controller (110) according to this aspect determines in the determination operation that the gas sensor (92) is not normal, satisfaction of the re-determination condition where "the predetermined period of time has elapsed since the supply of outdoor air to the gas sensor (92) is temporarily stopped," or "the measured value obtained by the oxygen sensor (91) falls within the predetermined range" allows the determination operation to be again performed.

—Feature (7) of Embodiment—

The inside air control system (30) according to this embodiment includes, as the gas sensor, the carbon dioxide sensor (92) that measures the concentration of carbon dioxide serving as a target gas, and performs the carbon dioxide control operation as the concentration control operation to control the concentration of carbon dioxide in the inside air based on the measured value obtained by the carbon dioxide sensor (92). This inside air control system (30) includes the oxygen sensor (91) that measures the concentration of oxygen contained in inside air, and performs the oxygen control operation to control the concentration of oxygen in the inside air based on the measured value obtained by the oxygen sensor (91). If the measured value obtained by the carbon dioxide sensor (92), which serves as the gas sensor, falls outside the normal range, the controller (110) disables only the carbon dioxide control operation among the carbon dioxide control operation and the oxygen control operation.

The inside air control system (30) according to this embodiment includes the carbon dioxide sensor (92) and the oxygen sensor (91), and performs the carbon dioxide control operation and the oxygen control operation. If the measured value obtained by the carbon dioxide sensor (92), which serves as the gas sensor, falls outside the normal range, the controller (110) according to this embodiment disables the inside air control system (30) to perform the carbon dioxide control operation, while allowing the inside air control system (30) to perform the oxygen control operation. Thus, according to this embodiment, even while the measured value obtained by the carbon dioxide sensor (92) is outside the normal range, the oxygen concentration of the inside air can be maintained within the target range, and the composition of the inside air can be as close to a target composition as possible.

—Feature (8) of Embodiment—

If the controller (110) of the inside air control system (30) according to this embodiment determines in the determination operation that the carbon dioxide sensor (92), which serves as the gas sensor, is normal, the controller (110) enables the carbon dioxide control operation.

If the controller (110) of the inside air control system (30) according to this embodiment determines in the determination operation that the carbon dioxide sensor (92) is normal, the controller (110) again allows the carbon dioxide control operation disabled while the measured value obtained by the carbon dioxide sensor (92) is outside the normal range. Thus, in this case, the inside air control system (30) can execute the carbon dioxide control operation as necessary.

As can be seen, even after the measured value obtained by the carbon dioxide sensor (92) has fallen outside the normal range, and has thus disabled the carbon dioxide control operation, if the controller (110) determines that the carbon dioxide sensor (92) is normal, the inside air control system (30) can execute the carbon dioxide control operation. Thus, if the carbon dioxide sensor (92) is determined to be normal, the state of the inside air control system (30) can be returned from the state where among the oxygen concentration and carbon dioxide concentration of the inside air, only the carbon dioxide concentration is controllable to the state where both the oxygen concentration and carbon dioxide concentration of the inside air is controllable. Thus, this embodiment can prevent a situation where although the carbon dioxide sensor (92) is normal, the carbon dioxide concentration of the inside air is not controllable from continuing for a long period of time, and can reliably keep the cargos (6) fresh.

—Feature (9) of Embodiment—

During the concentration control operation, the controller (110) of the inside air control system (30) according to this embodiment performs the calibration operation at predetermined time intervals. In the calibration operation, outdoor air is supplied through the outdoor air supply passage (255, 281) to the gas sensor (92) to calibrate the gas sensor (92).

While the inside air control system (30) according to this embodiment is executing the concentration control operation, the controller (110) of the inside air control system (30) performs the calibration operation to calibrate the gas sensor (92) once every predetermined time interval (in this embodiment, every seven days). This can reduce the error of the measured value obtained by the gas sensor (92) to a low level, and allows the concentration of the target gas in the inside air to be maintained within an appropriate range.

—First Variation of Embodiment—In the inside air control system (30) according to this embodiment, a target gas sensor to undergo the calibration operation performed by the sensor calibrator (116) of the controller (110) and the sensor abnormality handling operation performed by the sensor abnormality handler (117) of the controller (110) should not be limited to the carbon dioxide sensor (92). This gas sensor may be an oxygen sensor that measures the oxygen concentration of a target gas to be measured.

In many cases, vegetables, and fruits, which are a kind of plants, produce ethylene gas. Ethylene gas functions to hasten ripening of vegetables and fruits. Thus, to keep vegetables and fruits fresh, it is recommended that the concentration of ethylene gas in inside air be reduced to a low level. Thus, the inside air control system (30) includes an ethylene sensor that measures the concentration of ethylene gas in the inside air, and may be configured to perform an operation for reducing the concentration of ethylene gas in the inside air to a value less than or equal to a predetermined value. In this case, an ethylene sensor that measures the ethylene concentration of a measurement target gas, such as inside air, may be used as the target gas sensor to undergo the calibration operation performed by the sensor calibrator (116) and the sensor abnormality handling operation performed by the sensor abnormality handler (117).

The refrigerant circuit (11) of the container refrigerator (10) may be filled with a combustible refrigerant, for example, a combustible refrigerant R32. In this case, damage to the refrigerant circuit (11) may cause such a combustible refrigerant to leak into the shipping container (1). To address this leakage, the inside air control system (30) includes a refrigerant sensor that measures the refrigerant concentration, and if a measured value obtained by the refrigerant sensor exceeds a predetermined reference value, the inside air control system (30) may be instructed to execute an operation for discharging the refrigerant to the outside of the shipping container (1). In this case, a refrigerant sensor that measures the refrigerant concentration of a target gas, such as inside air, may be used as the target gas sensor to undergo the calibration operation performed by the sensor calibrator (116) and the sensor abnormality handling operation performed by the sensor abnormality handler (117).

—Second Variation of Embodiment—

The inside air control system (30) according to this embodiment may be installed in a stationary refrigerator or freezer. The inside air control system (30) according to this embodiment may be installed in a refrigerated/reefer container for overland transportation to be transported by truck, rail, and other means. The inside air control system (30) according to this embodiment may be installed in a refrigerated/reefer truck including a box defining a cargo space and integrated with the chassis of the truck.

While the embodiment and variations thereof have been described above, it will be understood that various changes in form and details may be made without departing from the spirit and scope of the claims. The foregoing embodiment and variations thereof may be combined or replaced with each other without deteriorating the intended functions of the present disclosure.

INDUSTRIAL APPLICABILITY

As can be seen from the foregoing description, the present disclosure is useful for an inside air control system.

EXPLANATION OF REFERENCES

1 Shipping Container (Storage)
30 Inside Air Control System
91 Oxygen Sensor
92 Carbon Dioxide Sensor (Gas Sensor)
110 Controller
255 First Bypass Pipe (Outdoor Air Supply Passage)
281 Measurement Connection Pipe (Outdoor Air Supply Passage)

The invention claimed is:

1. An inside air control system comprising:
a gas sensor (92) configured to measure a concentration of a target gas contained in inside air in a storage (1),
the inside air control system performing a concentration control operation to control the concentration of the target gas in the inside air based on a measured value obtained by the gas sensor (92),
the inside air control system further comprising:
an outdoor air supply passage (255, 281) through which outdoor air is to be supplied to the gas sensor (92); and
a controller (110) configured to perform a determination operation if the measured value obtained by the gas sensor (92) returns to a predetermined normal range after falling outside the normal range, the determination operation being performed to supply outdoor air through the outdoor air supply passage (255, 281) to the gas sensor (92) to determine whether or not the gas sensor (92) is normal.

2. The inside air control system of claim 1, wherein
if the measured value obtained by the gas sensor (92) falls within a predetermined reference range including a concentration of the target gas in outdoor air that is being supplied to the gas sensor (92), the controller (110) determines in the determination operation that the gas sensor (92) is normal, and if the value measured by the gas sensor (92) falls outside the reference range, the controller (110) determines that the gas sensor (92) is not normal.

3. The inside air control system of claim 1, wherein
if the controller (110) determines in the determination operation that the gas sensor (92) is normal, the controller (110) calibrates the gas sensor (92) based on the measured value obtained by the gas sensor (92) to which outdoor air is being supplied.

4. The inside air control system of claim 1, wherein
if the measured value obtained by the gas sensor (92) falls outside the predetermined normal range, the controller (110) stops the concentration control operation.

5. The inside air control system of claim 1, wherein
if the controller (110) determines in the determination operation that the gas sensor (92) is not normal, the controller (110) temporarily stops supply of outdoor air to the gas sensor (92), and if a predetermined re-determination condition is thereafter satisfied, the controller (110) again performs the determination operation.

6. The inside air control system of claim 5 further comprising:
in addition to the gas sensor (92), an oxygen sensor (91) configured to measure a concentration of oxygen contained in the inside air,
an oxygen control operation being performed to control the concentration of oxygen in the inside air based on a measured value obtained by the oxygen sensor (91),
the re-determination condition for the controller (110) being a condition where a predetermined period of time has elapsed since supply of outdoor air to the gas sensor (92) is temporarily stopped, or the measured value obtained by the oxygen sensor (91) falls within a predetermined range.

7. The inside air control system of claim 1, wherein
a carbon dioxide sensor (92) configured to measure a concentration of carbon dioxide serving as the target gas is used as the gas sensor (92), a carbon dioxide control operation is performed as the concentration control operation to control the concentration of carbon dioxide in the inside air based on a measured value obtained by the carbon dioxide sensor (92),
the inside air control system further comprises an oxygen sensor (91) configured to measure a concentration of oxygen contained in the inside air, an oxygen control operation is performed to control the concentration of oxygen in the inside air based on a measured value obtained by the oxygen sensor (91), and
if the measured value obtained by the carbon dioxide sensor (92), which serves as the gas sensor, falls outside the normal range, the controller (110) disables only the carbon dioxide control operation among the carbon dioxide control operation and the oxygen control operation.

8. The inside air control system of claim 7, wherein
if the controller (110) determines in the determination operation that the carbon dioxide sensor (92), which serves as the gas sensor, is normal, the controller (110) enables the carbon dioxide control operation.

9. The inside air control system of claim 1, wherein
during the concentration control operation, the controller (110) performs a calibration operation at predetermined time intervals, the calibration operation being performed to supply outdoor air through the outdoor air supply passage (255, 281) to the gas sensor (92) to calibrate the gas sensor (92).

* * * * *